(12) United States Patent
Botich et al.

(10) Patent No.: US 7,691,083 B2
(45) Date of Patent: *Apr. 6, 2010

(54) FLUID COLLECTION DEVICE WITH CAPTURED RETRACTABLE NEEDLE

(75) Inventors: Michael J. Botich, Oxnard, CA (US); Thor R. Halseth, Simi Valley, CA (US)

(73) Assignee: MDC Investmant Holdings, Inc., Salt Lake City, UT (US)

( * ) Notice: Subject to any disclaimer, the term of this patent is extended or adjusted under 35 U.S.C. 154(b) by 1195 days.

This patent is subject to a terminal disclaimer.

(21) Appl. No.: 10/698,763

(22) Filed: Oct. 31, 2003

(65) Prior Publication Data

US 2004/0092872 A1 May 13, 2004

Related U.S. Application Data

(63) Continuation of application No. 09/685,247, filed on Oct. 10, 2000, now Pat. No. 6,641,555, which is a continuation-in-part of application No. 09/191,044, filed on Nov. 12, 1998, now abandoned.

(60) Provisional application No. 60/065,348, filed on Nov. 12, 1997, provisional application No. 60/081,135, filed on Apr. 9, 1998, provisional application No. 60/084,814, filed on May 8, 1998.

(51) Int. Cl.
A61M 5/00 (2006.01)
(52) U.S. Cl. ........................ 604/110; 604/198
(58) Field of Classification Search ................. 604/110, 604/198, 164.12, 192
See application file for complete search history.

(56) References Cited

U.S. PATENT DOCUMENTS 3,463,152 A  8/1969  Sorenson
4,409,990 A  10/1983  Mileikowsky
4,425,120 A  1/1984  Sampson et al.
4,517,978 A  5/1985  Levin et al.
4,573,976 A  3/1986  Sampson et al.
4,631,057 A  12/1986  Mitchell
4,643,200 A  2/1987  Jennings, Jr.
4,747,831 A  5/1988  Kulli
4,752,290 A  6/1988  Schramm
4,758,231 A  7/1988  Haber et al.
4,813,426 A  3/1989  Haber et al.
4,822,343 A  4/1989  Beiser
4,826,491 A  5/1989  Schramm
4,841,985 A  6/1989  Wanamaker
4,850,374 A  7/1989  Diaz-Ramos
4,850,977 A  7/1989  Bayless
4,892,107 A  1/1990  Haber
4,900,307 A  2/1990  Kulli
4,915,702 A  4/1990  Haber
4,931,048 A  6/1990  Lopez
4,943,283 A  7/1990  Hogan
4,947,863 A  8/1990  Haber et al.
4,995,870 A  2/1991  Baskas (Continued)

FOREIGN PATENT DOCUMENTS

| JP | 59-160441 | 9/1984 |
| JP | 2-502076 | 7/1990 |
| JP | 7-24307 | 5/1995 |
| JP | 9-506533 | 6/1997 |
| WO | WO 89/04678 | 6/1989 |
| WO | WO 95/16389 | 6/1995 |

*Primary Examiner*—Nicholas D Lucchesi
*Assistant Examiner*—Theodore J Stigell
(74) *Attorney, Agent, or Firm*—Rutan & Tucker, LLP

(57) ABSTRACT

A fluid transfer device includes a tube holder, a fluid container, a double ended needle with forward sharpened tip, and rearward sharpened tip. Fluid is withdrawn or injected into a patient from the tip, and into fluid contained.

18 Claims, 18 Drawing Sheets

U.S. PATENT DOCUMENTS

| | | |
|---|---|---|
| 5,024,660 A | 6/1991 | McNaughton |
| 5,041,088 A | 8/1991 | Ritson et al. |
| 5,069,225 A | 12/1991 | Okamura |
| 5,070,885 A | 12/1991 | Bonaldo |
| 5,112,307 A | 5/1992 | Haber et al. |
| 5,147,329 A | 9/1992 | Brannon |
| 5,178,157 A | 1/1993 | Fanlo |
| 5,186,712 A | 2/1993 | Kelso et al. |
| 5,188,599 A | 2/1993 | Botich et al. |
| 5,250,026 A | 10/1993 | Ehrlich et al. |
| 5,360,408 A | 11/1994 | Vaillancourt |
| 5,395,347 A | 3/1995 | Blecher et al. |
| 5,403,286 A | 4/1995 | Lockwood, Jr. |
| 5,411,487 A | 5/1995 | Castagna |
| 5,423,758 A | 6/1995 | Shaw |
| 5,480,385 A | 1/1996 | Thorne et al. |
| 5,487,734 A | 1/1996 | Thorne et al. |
| 5,526,853 A | 6/1996 | McPhe et al. |
| 5,527,290 A | 6/1996 | Zadini et al. |
| 5,542,927 A | 8/1996 | Thorne et al. |
| 5,562,629 A | 10/1996 | Haughton et al. |
| 5,571,134 A | 11/1996 | Yoon |
| 5,575,777 A | 11/1996 | Cover et al. |
| 5,613,500 A | 3/1997 | Bishop |
| 5,620,008 A | 4/1997 | Shinar et al. |
| 5,685,855 A | 11/1997 | Erskine |
| 5,685,863 A | 11/1997 | Botich et al. |
| 5,746,215 A | 5/1998 | Manjarrez |
| 5,755,709 A | 5/1998 | Cuppy |
| 5,779,679 A * | 7/1998 | Shaw .................. 604/158 |
| 5,779,683 A | 7/1998 | Meyer |
| 5,797,880 A | 8/1998 | Erskine |
| 5,800,395 A | 9/1998 | Botich et al. |
| 5,810,775 A | 9/1998 | Shaw |
| 5,951,515 A | 9/1999 | Osterlind |
| 6,210,371 B1 * | 4/2001 | Shaw .................. 604/164.08 |
| 6,398,743 B1 * | 6/2002 | Halseth et al. .......... 600/585 |
| 6,786,875 B2 * | 9/2004 | Barker et al. .......... 600/585 |
| 7,097,633 B2 * | 8/2006 | Botich et al. .......... 604/110 |
| 7,153,276 B2 * | 12/2006 | Barker et al. .......... 600/576 |

* cited by examiner

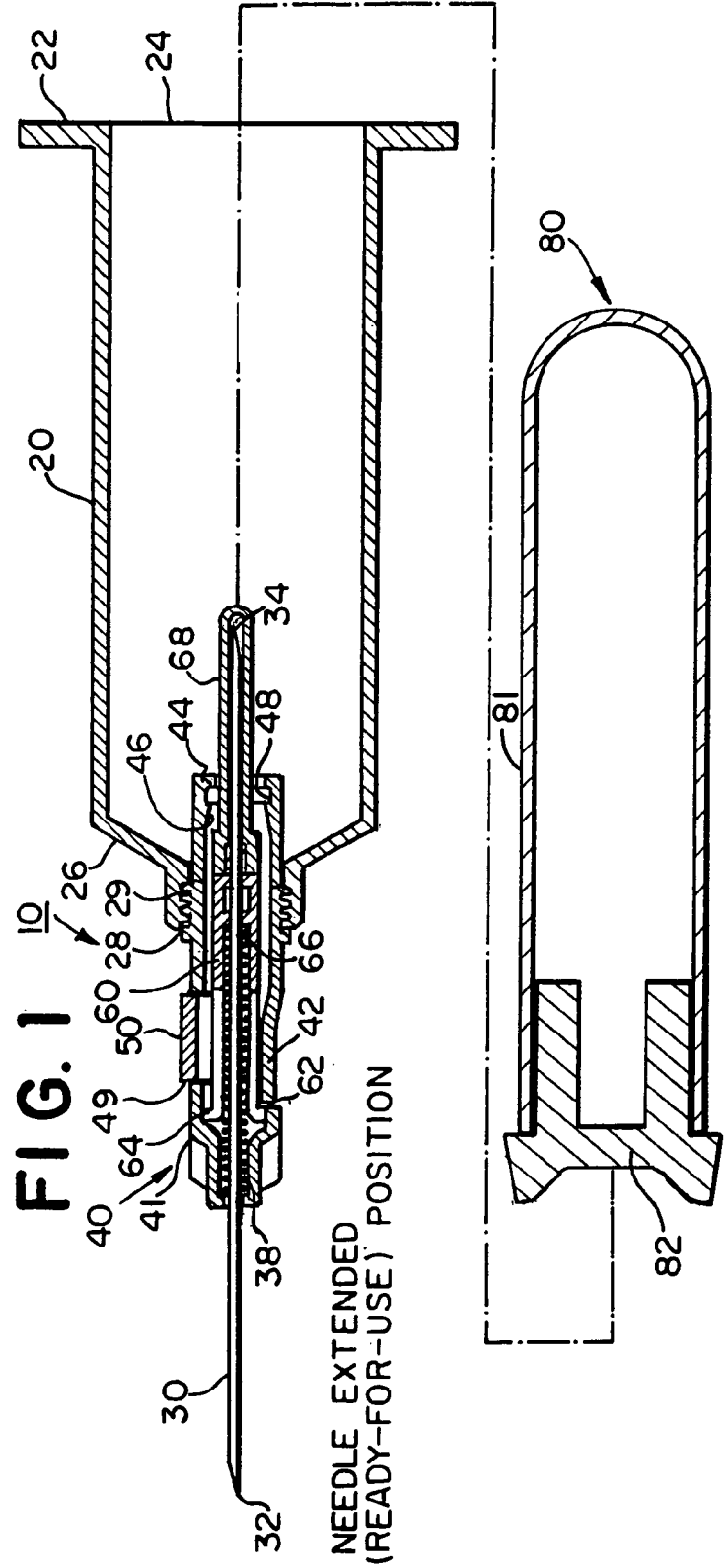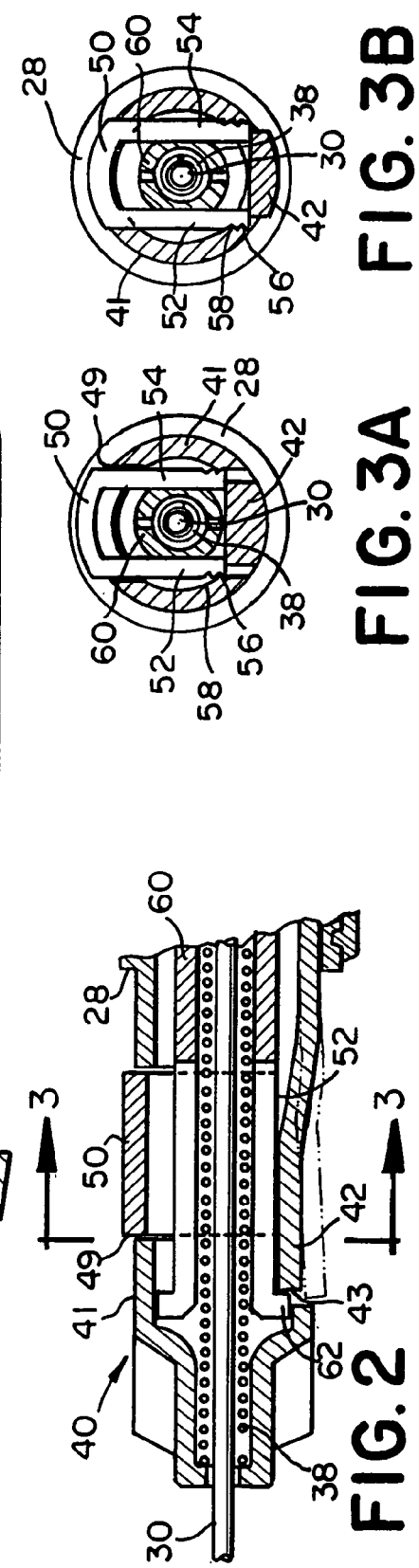

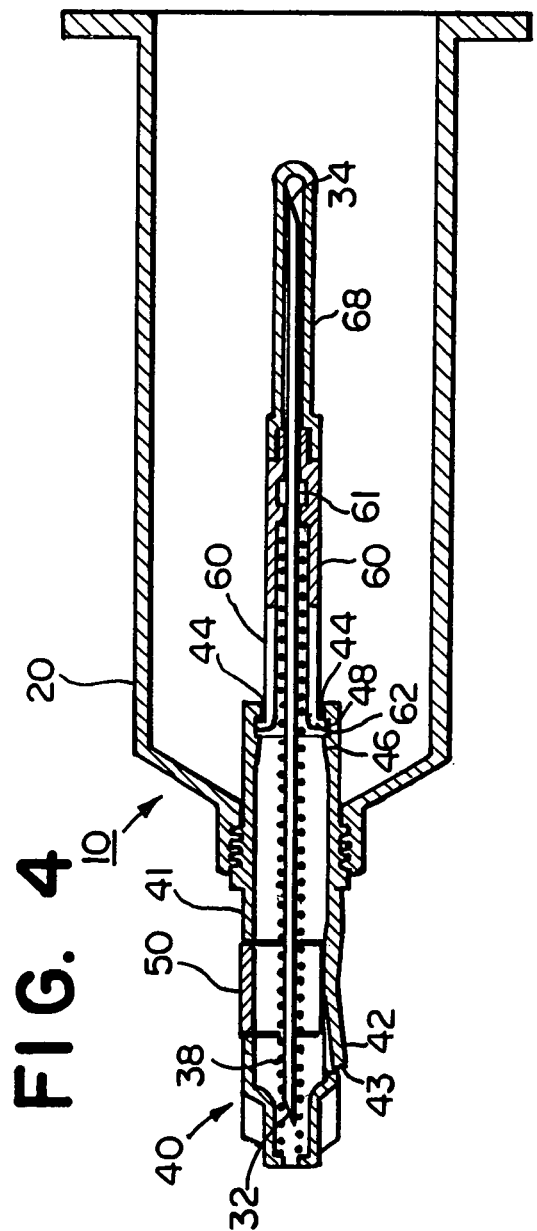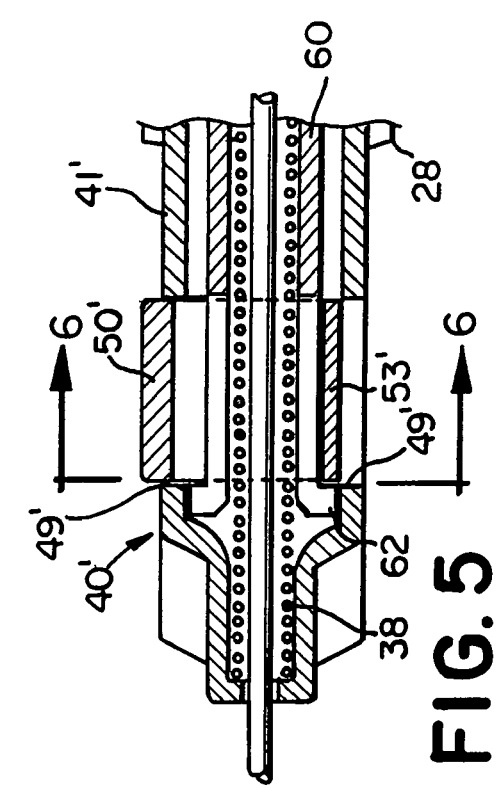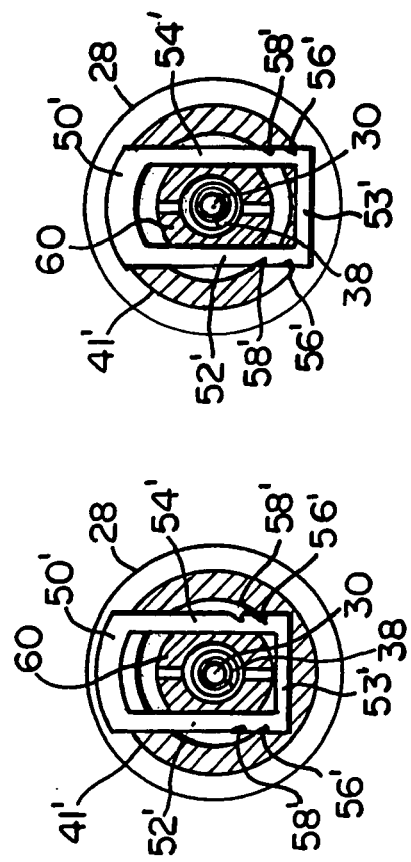

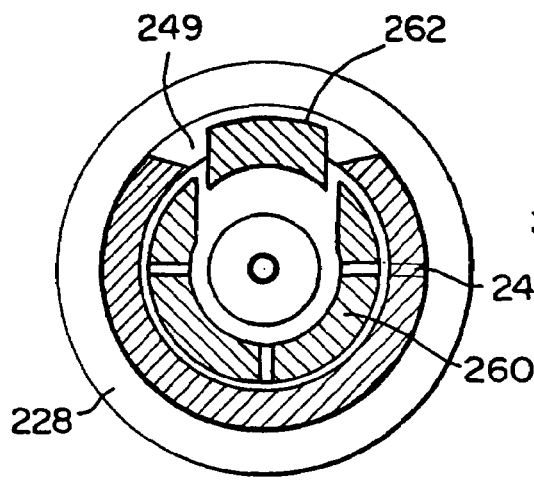 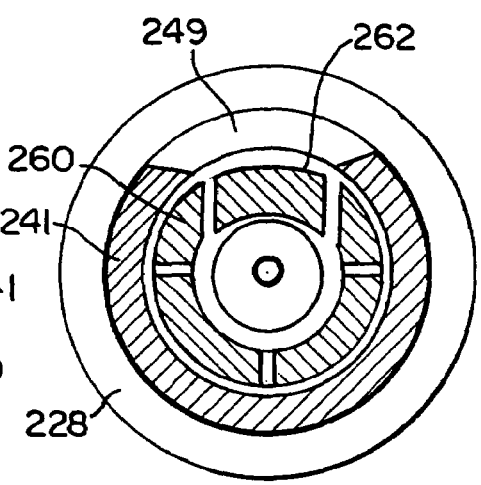
FIG.11A  FIG.11B
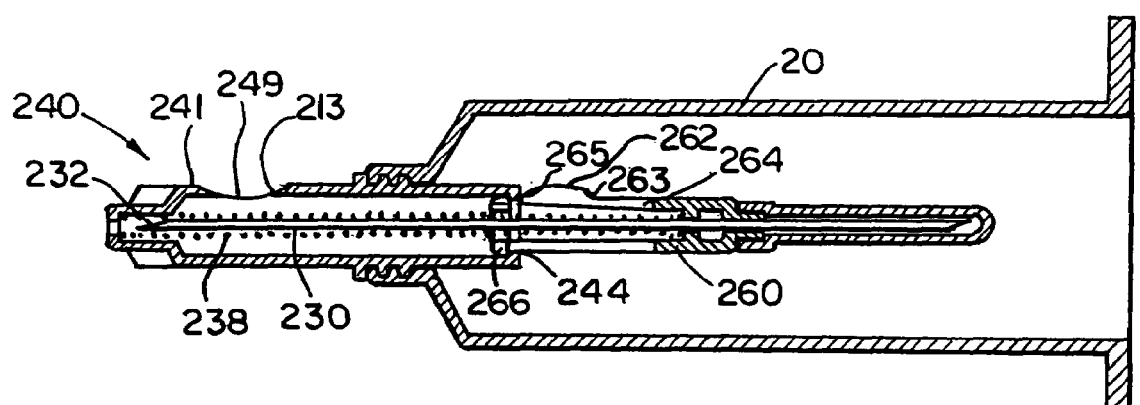
FIG. 12

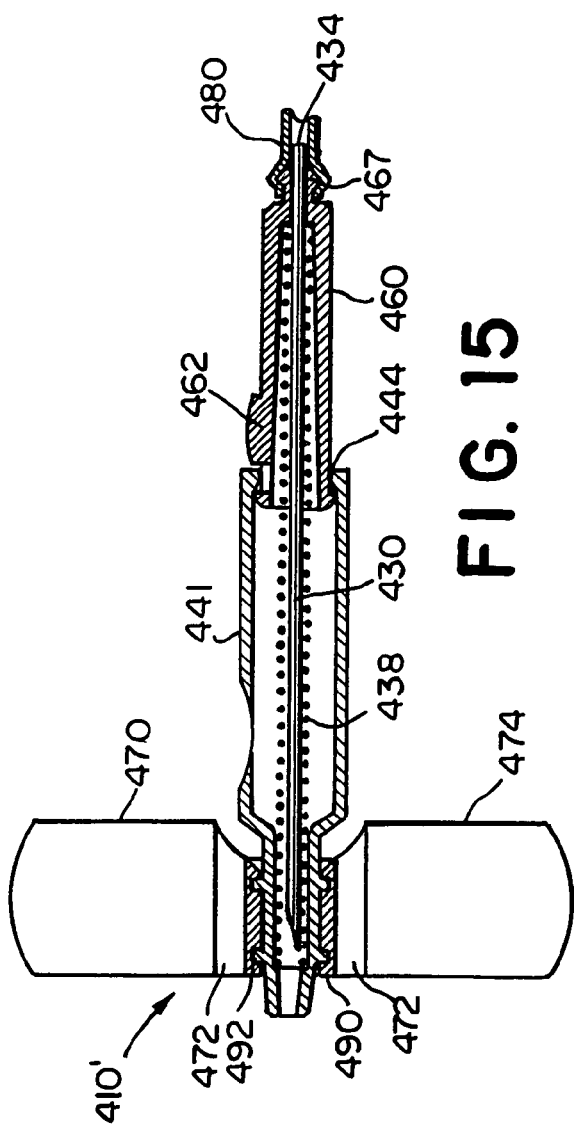
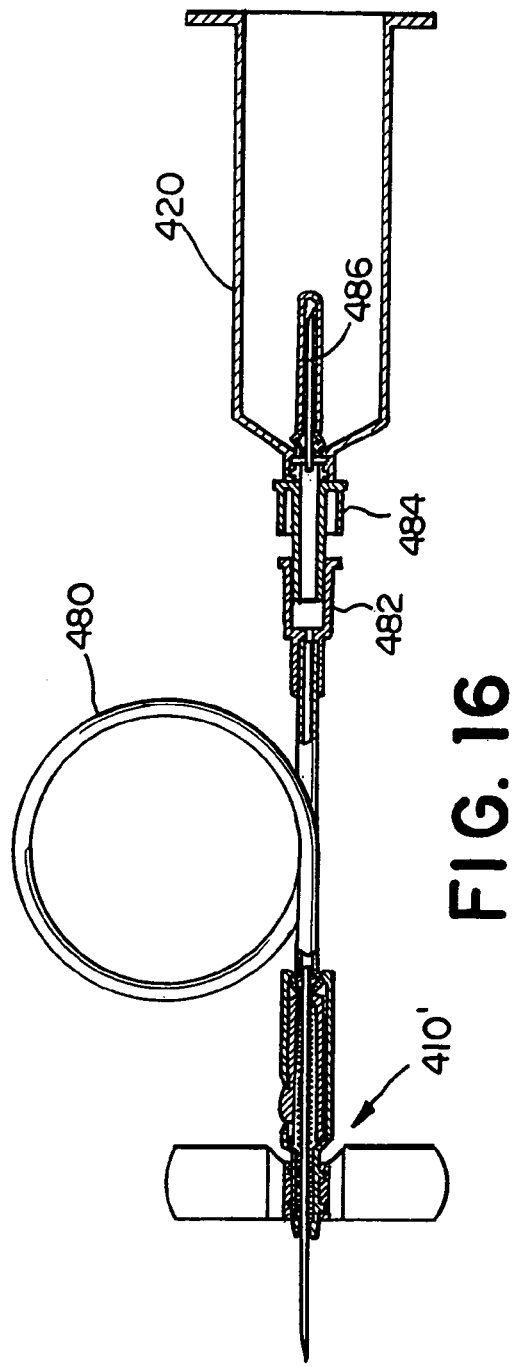

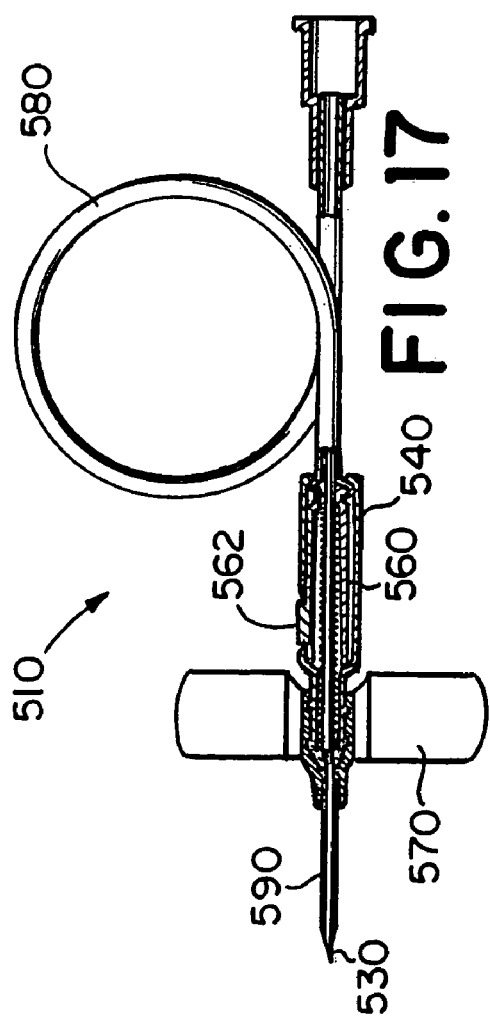
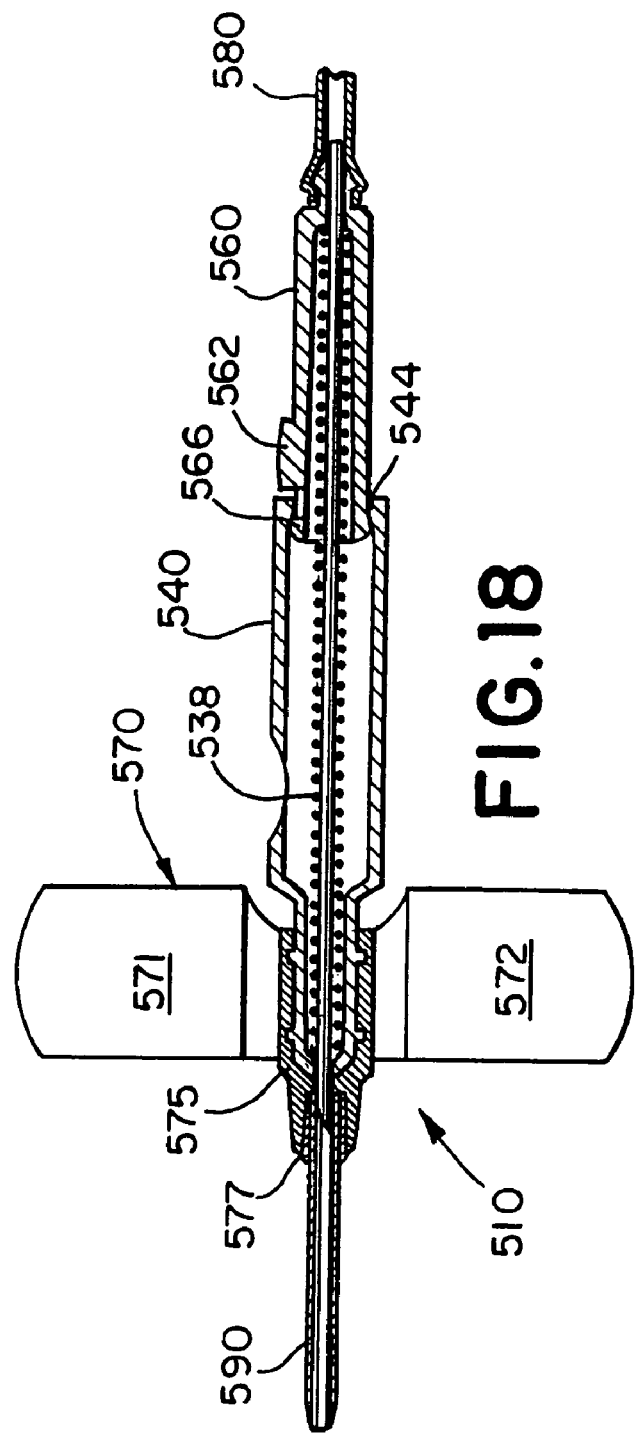

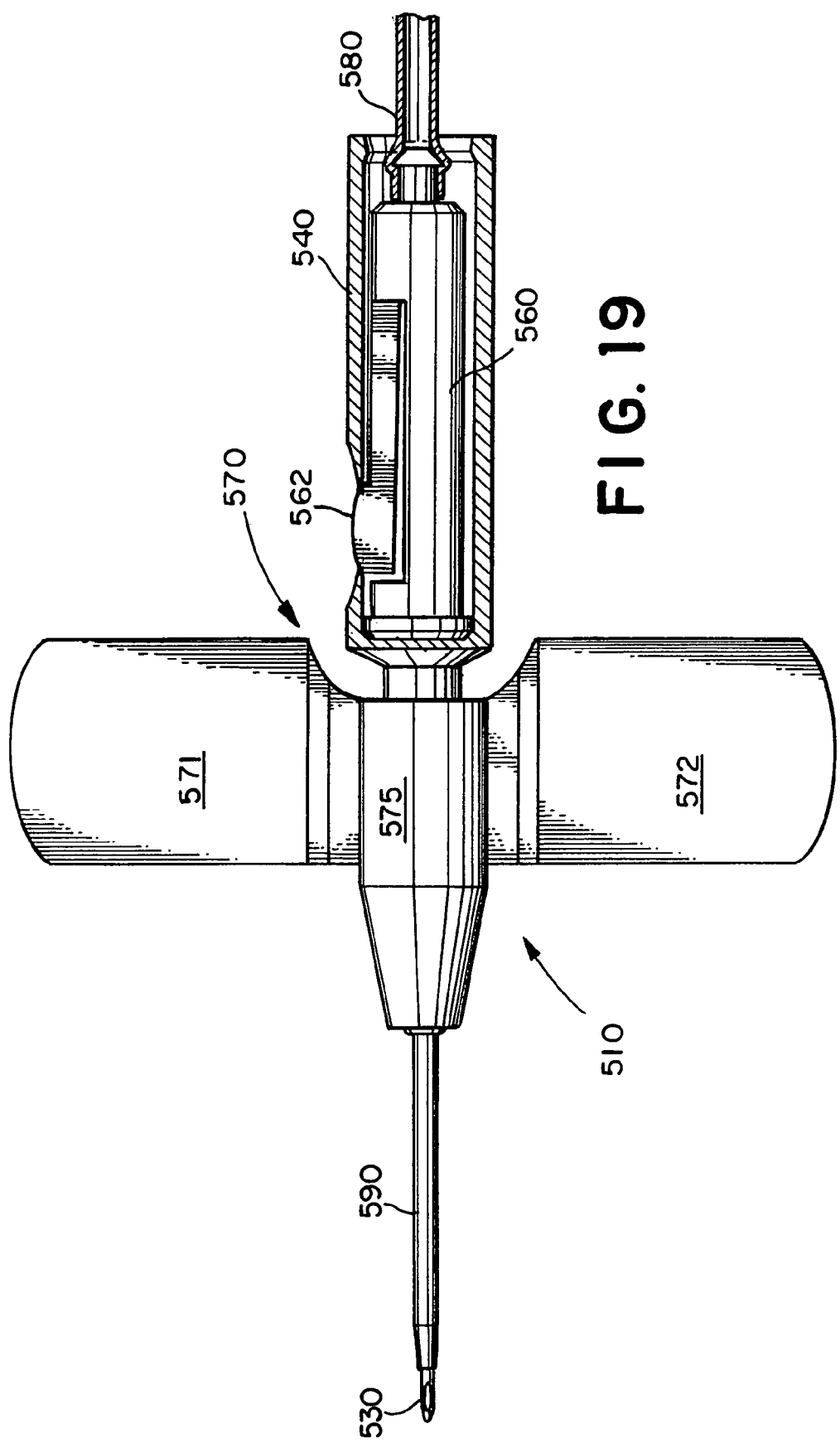

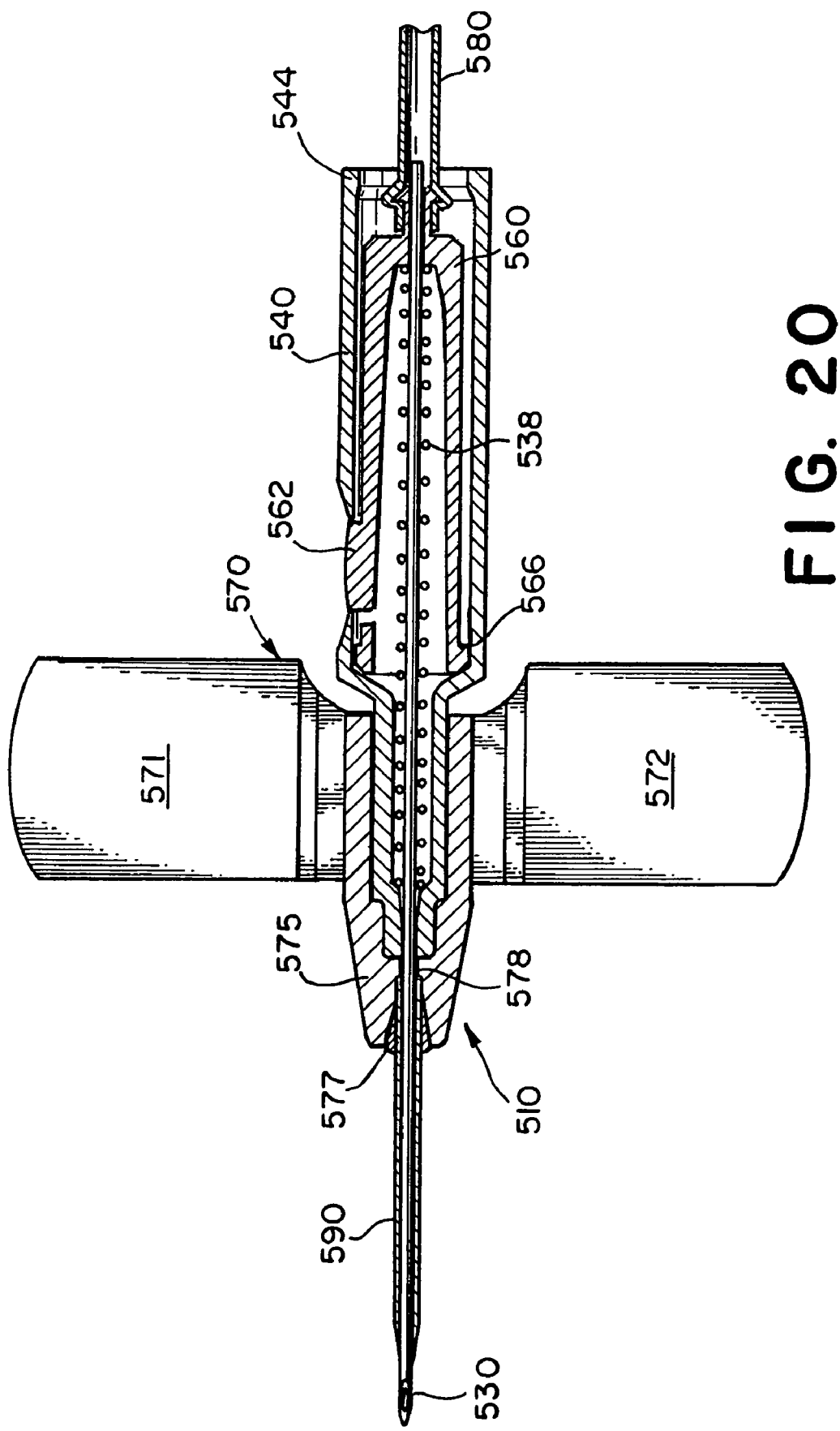

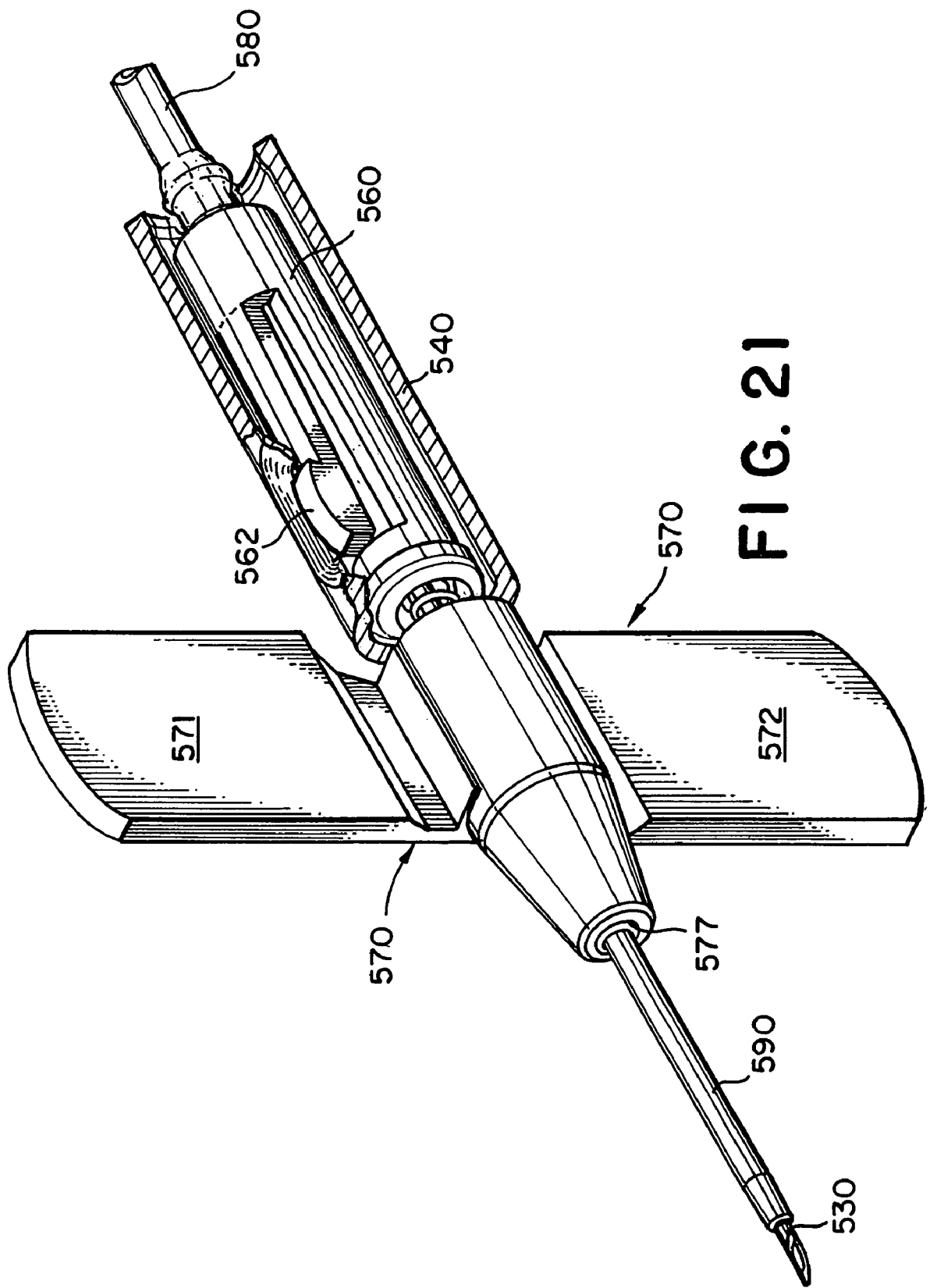

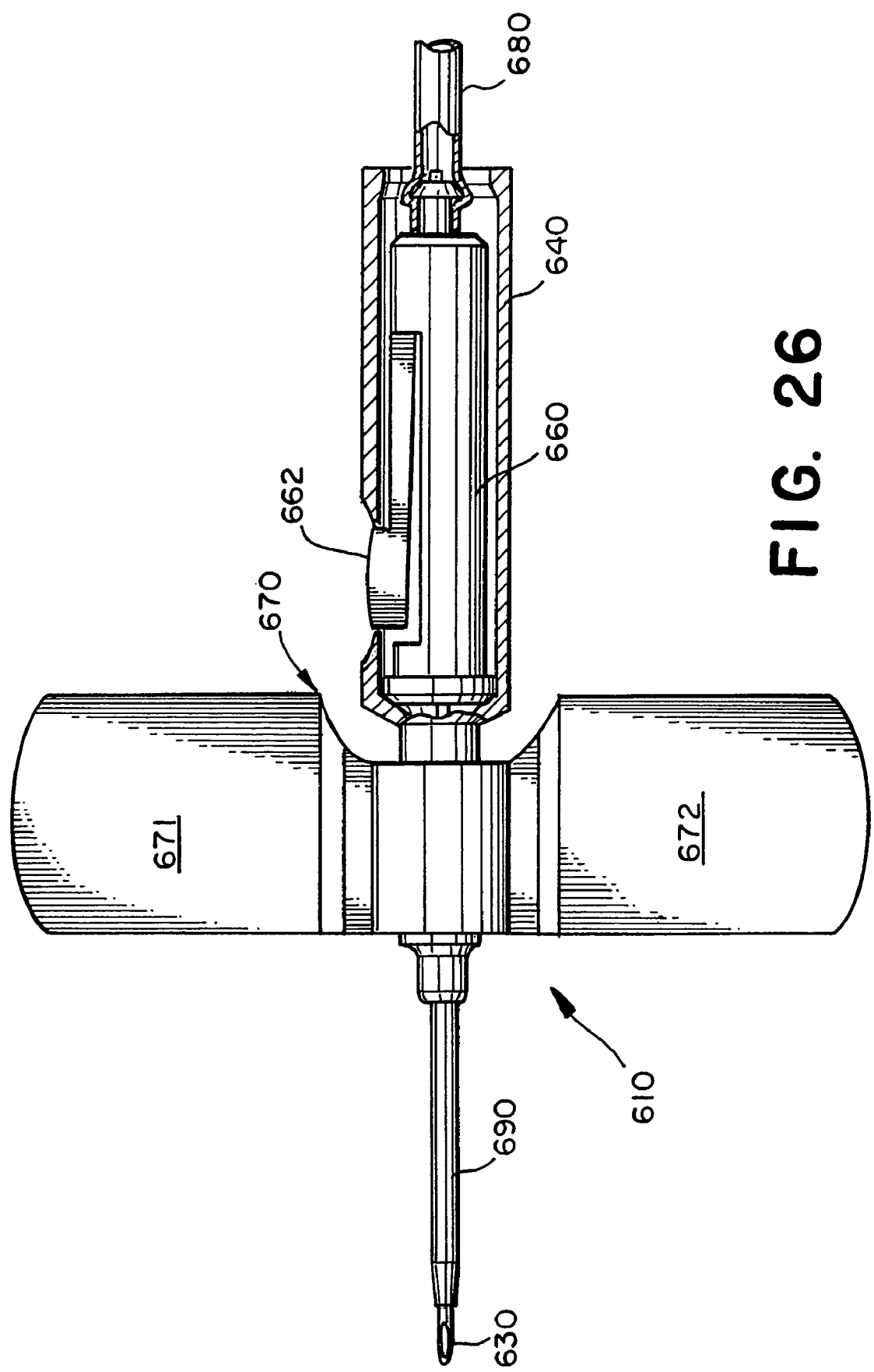

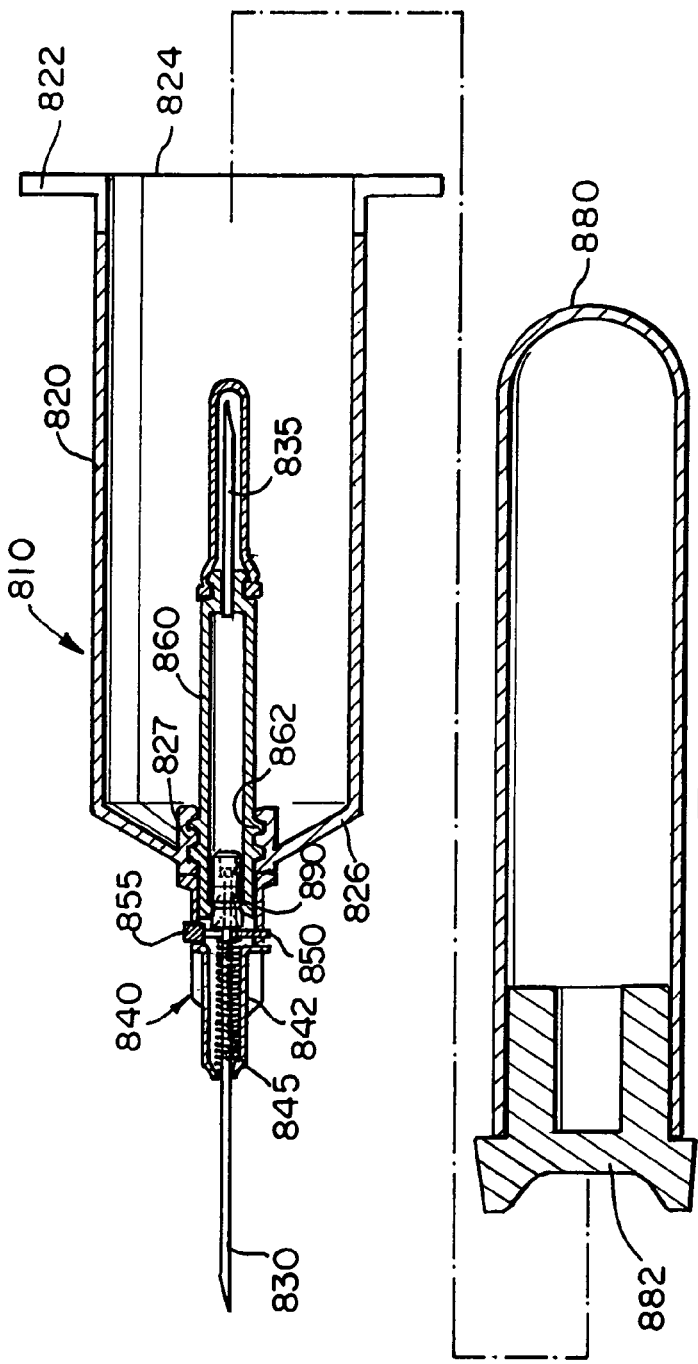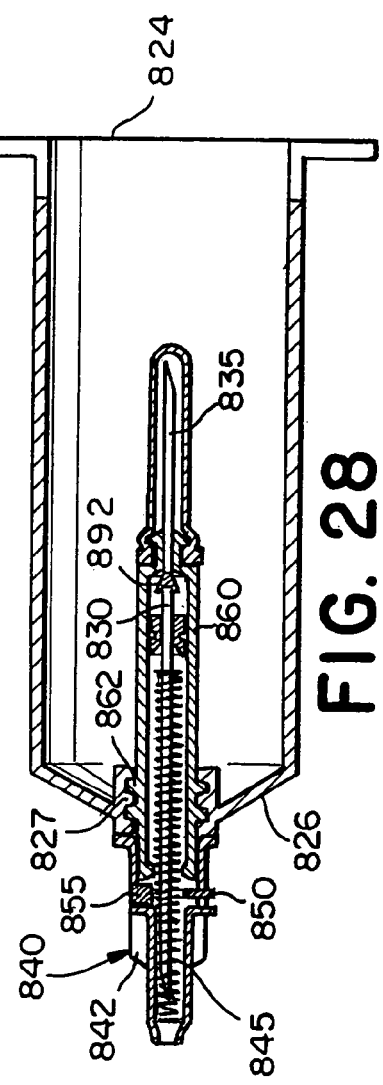

FLUID COLLECTION DEVICE WITH CAPTURED RETRACTABLE NEEDLE

RELATED CASES

This application is a continuation of U.S. patent application Ser. No. 09/685,247 filed Oct. 10, 2000 now U.S. Pat. No. 6,641,555, which is a continuation-in-part application of U.S. patent application Ser. No. 09/191,044 filed Nov. 12, 1998 now abandoned, which claims priority to U.S. Provisional Application Nos. 60/065,348 filed Nov. 12, 1997, 60/081,135 filed Apr. 9, 1998, and 60/084,814 filed May 8, 1998. Each of the foregoing applications are hereby incorporated herein by reference.

FIELD OF THE INVENTION

The present invention relates to a fluid transfer device for transferring fluid to or from a patient, and more particularly to a fluid transfer device having a retractable needle.

BACKGROUND OF THE INVENTION

Various types of medical devices employ a needle for piercing the skin of a patient for diagnostic or therapeutic purposes. One such fluid transfer device is a fluid collection device which includes a needle for piercing a blood vessel or other part of the patient to allow a fluid, for example, blood, to be sampled from a patient. When the needle is inserted into the patient, blood or other fluid is withdrawn through the needle, for example, into a vacuum collection tube. Handling of such needle-bearing medical devices after the needle is withdrawn from the patient can result in transmission of various pathogens, most notably human immune virus (HIV), thereby exposing medical personnel and possibly others to serious or fatal illness due to an inadvertent needle stick or scratch.

After use of a needle-bearing medical device, it is desirable to have an easily usable feature for retracting the needle into a housing to avoid contact with the small volume of contaminated fluid or blood that may remain on or inside the needle. It is further desirable that it be made difficult for personnel to accidentally or intentionally re-extend the needle from within the housing.

Accordingly, there is a need for a fluid transfer device that not only retracts the needle following its use, but that also captures or positively retains the needle in the retracted position within the housing thereafter.

SUMMARY OF THE INVENTION

In light of the foregoing, the present invention provides a medical device having a hollow housing and a needle with a sharpened tip. The needle is operable between an extended and a retracted position. The sharpened tip projects forwardly from the housing in the extended position and the sharpened tip is enclosed within the housing in the retracted position. A biasing element biases the needle toward the retracted position. A needle retainer releasably retains the needle in the extended position. An actuator actuates the needle retainer to release the needle so that the biasing element propels the needle rearwardly toward the retracted position. A rearward stop connected with the needle is operable to retain the needle against continued rearward displacement after the needle is retracted. A forward stop connected with the needle is operable to retain the needle against forward displacement after the needle is retracted.

BRIEF DESCRIPTION OF THE DRAWING

FIG. 1 is a sectional view of a fluid transfer device having a retractable needle showing the needle in an extended position;

FIG. 2 is an enlarged fragmentary sectional view of the device illustrated in FIG. 1;

FIG. 3A is a cross-sectional view of the device shown in FIG. 2 taken along the line 3-3;

FIG. 3B is a cross-sectional view of the device illustrated in FIG. 3A, showing the device after actuation of needle retraction;

FIG. 4 is a sectional view of the device shown in FIG. 1, showing the device after actuation of needle retraction;

FIG. 5 is a sectional view of an alternative embodiment of a fluid transfer device having a retractable needle;

FIG. 6A is a cross-sectional view of the device shown in FIG. 5 taken along the line 6-6;

FIG. 6B is a cross-sectional view of the device illustrated in FIG. 6A, showing the device after actuation of needle retraction;

FIG. 11A is a cross-sectional view of the device shown in FIG. 10 taken along the line 11-11;

FIG. 11B is a cross-sectional view of the device illustrated in FIG. 11A, showing the device after actuation of needle retraction;

FIG. 12 is a sectional view of the device shown in FIG. 10, showing the device after actuation of needle retraction;

FIG. 15 is a sectional diagram of the device shown in FIG. 14A, showing the device after actuation of needle retraction;

FIG. 16 is a side elevational view of the device shown in FIG. 14A, partially in section, in combination with a tube holder;

FIG. 17 is a side elevational view, partially in section of a fluid transfer device with a fixed catheter;

FIG. 18 is an enlarged fragmentary sectional view of the device illustrated in FIG. 17, with the needle in a retracted position;

FIG. 19 is an enlarged fragmentary side elevational view of the device shown in FIG. 17;

FIG. 20 is an enlarged fragmentary sectional view of the device illustrated in FIG. 17;

FIG. 21 is an enlarged fragmentary perspective view of the device illustrated in FIG. 17;

FIG. 26 is a side elevational view of the device illustrated in FIG. 23;

FIG. 27 is a side view of a fluid collection device having a retractable insertion needle, with the insertion needle projecting forwardly prior to use;

FIG. 28 is a side elevational view of the fluid collection device illustrated in FIG. 27, showing the insertion needle retracted after use;

DETAILED DESCRIPTION OF THE PREFERRED EMBODIMENTS

Figure 7:
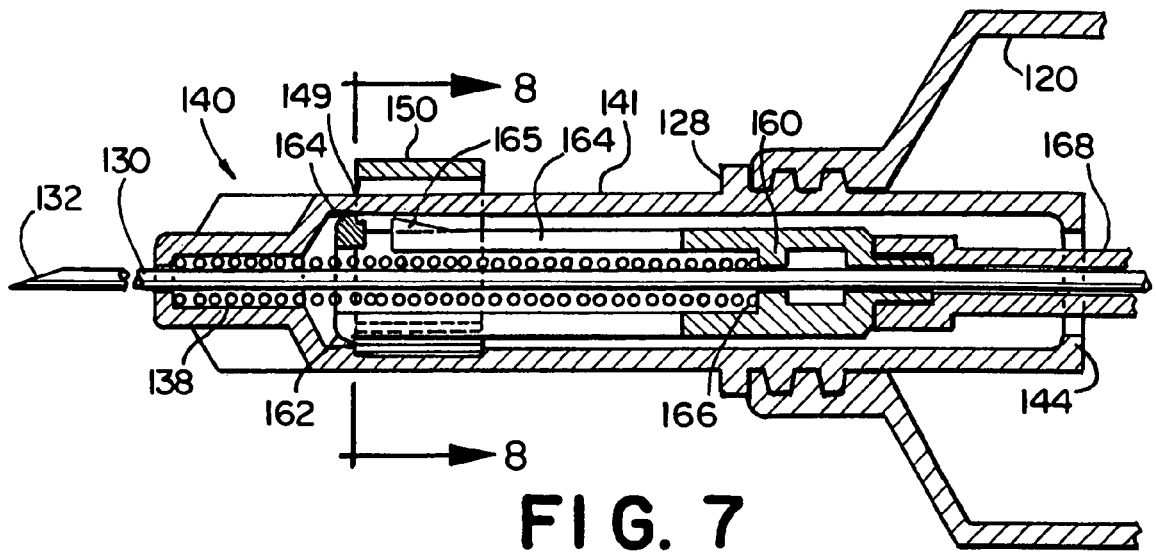
FIG. 7 is a sectional view of another alternative embodiment of a fluid transfer device having a retractable needle.

The following detailed description of the preferred embodiments according to the present invention will be better understood when read in conjunction with the accompanying drawing described above.

Referring now to FIGS. 1-4 generally and to FIG. 1 specifically, a fluid transfer device 10 is illustrated. The device 10 includes a tube holder 20 for receiving a fluid container 80. The device includes a double-ended needle 30 having a forward sharpened tip 32 and a rearward sharpened tip 34. The forward tip 32 is insertable into a patient for withdrawing or injecting fluid. The rearward tip is operable to pierce a seal in the fluid container 80. After use the needle 30 is retractable into the tube holder 20 to enclose the forward tip 32.

In FIG. 1 fluid transfer device 10 has a hollow cylindrical tube holder 20 having a rearward end 24 which is adapted to receive a fluid collection container such as vacuum tube 80. Fluid collection container 80 ordinarily includes a glass or plastic container 81 and a resilient stopper 82 forming a pierceable end on the container 80. Tube holder 20 further includes a circumferential flange 22 providing a convenient place for medical personnel to rest their fingers when using fluid collection device 10 including the insertion and removal of vacuum tubes 80. The forward portion 26 of housing 20 is tapered to a reduced diameter portion preferably having an internally threaded portion 29 for threadedly engaging a needle assembly 40 which will now be described.

Needle assembly 40 includes a double-ended needle 30 having a forward needle end 32 for piercing a patient for the collection of fluid and has a rearward end adapted for transferring fluid, such as needle end 34 for piercing the pierceable end 82 of fluid collection container 80 when the container is inserted into the rearward end 24 of tube holder 20. Needle assembly 40 includes a generally cylindrical or barrel-shaped housing 41 in which doubled-ended needle 30 is retractably mounted. Needle assembly 40 preferably includes external threads 28 which engage corresponding internal threads 29 at the forward end of tube holder 20.

Double-ended needle 30 is fixedly mounted to a carrier such as a needle tube 60 which is slidably mounted within the barrel 41 of needle assembly 40. Double-ended needle 30 may be affixed to needle tube 60, for example, by a friction fit or by adhesive bonding or by insert molding, such as may be applied through bonding port 61. In the present instance, the needle 30 is bonded to the tube 60. A flexible rubber or plastic boot 68 covers the rearward needle end 34 of double-ended needle 30 and is affixed to the rearward end of needle tube 60 for keeping needle end 34 clean and sterile prior to use, and for stopping the flow of body fluid out of needle end 34 when a collection tube 80 is not in place.

As may be seen in the enlarged portion of the embodiment of FIG. 1 shown in FIG. 2, coil spring 38 is compressed and bears against the forward end of barrel 41 of needle assembly 40 and against the bottom of the bore 66 in needle tube 60, thereby urging needle tube 60 and double-ended needle 30 rearward (to the right as shown in FIGS. 1-4). A flexible member 42 has an end 43 that engages a flange 62 on the needle tube 60 to retain the needle tube in a projecting position against the rearward bias of a spring 38.

Retraction of the needle 30 and needle tube 60 is actuated by an actuation button 50. The actuation button 50 is preferably circumferentially aligned with the bevel of needle end 32 as shown in FIG. 1. Referring now to FIGS. 2, 3A and 3B, actuation button 50 is positioned in transverse slot 49 in barrel 41 of needle assembly 40 for transverse motion for moving flexible member 42 radially outwardly, or downwardly from the perspective of FIGS. 1-4. The button 50 includes vertically disposed side members 52, 54. Prior to actuation, button 50 is held in the unactuated position by an indentation 56 on at least one of the side members 52, 54, which engages a lip on the interior of barrel 41. In this position, flexible member 42 engages flange 62 on the needle tube 60. When actuation button 50 is depressed, the downward motion is transmitted through button side members 52 and 54 to cause flexible member 42 to move radially outwardly, thereby disengaging end 43 of flexible member 42 from flange 62 of needle tube 60, and thereby permitting needle tube 60 and double-ended needle 30 to move rearward under the urging of spring 38. Subsequent to actuation, button 50 may be held in the actuated position by indentation 58 engaging the aforementioned feature on the interior of barrel 41, which may simply be a lip or an edge of transverse slot 49.

Following actuation of button 50 to release the engagement of end 43 of flexible member 42 and flange 62, needle tube 60 including double-ended needle 30 moves rearwardly into a retracted position in which the first needle end 32 of double-ended needle 30 is withdrawn into the housing provided by barrel 41 of the needle assembly 40, i.e. needle 30 is drawn into the housing, as shown in FIG. 4. The rearward end of barrel 41 includes an interior projecting flange or lip 44 which engages flange 62 to block further rearward motion of needle tube 60 under the urging of coil spring 38. Barrel 41 further includes a second interior projecting feature in flange or lip 46 which in cooperation with stopping lip 44 forms a groove 48 which engages or captures flange 62 of needle tube 60, thereby positively retaining needle tube 60 and therefore double-ended needle 30 in the retracted position.

Accordingly, flange 62 is an engaging feature that both holds double-ended needle 30 in the extended needle position from which it may be used for medical purposes and also retains double-ended needle 30 in its retracted needle position where it is relatively safe from accidental contact with or sticking of medical or other personnel. In this way, stopping lip 44 operates as a rearward stop limiting rearward displacement of the needle 30; and flange 46 operates as a forward stop limiting forward displacement of the needle after retraction.

Configured in this way, device 10 operates as follows. Needle assembly 40 which has front and rear protective caps installed to cover the front and rear needle ends 32, 34, respectively, of double-ended needle 30, is removed from its sterile packaging. The rear protective cap (not shown) is removed and needle assembly 40 is threaded into tube holder 20 by engaging threads 28, 29. The front protective cap (not shown) covers actuation button 50 to prevent retraction of double-ended needle 30. Thereafter, the front protective cap is removed and the front tip 32 of the needle 30 is inserted into a patient. A fluid collection container such as a vacuum tube 80 is then inserted into the open end 24 of the housing 20. The rear tip 34 of the needle pierces protective boot 68 and the resealable plug 82 of the vacuum tube 80 so that the vacuum tube is in fluid communication with the front tip 32 via double-ended needle 30. In this way, fluid flows from the needle 32 into the vacuum tube 80. After vacuum tube 80 is filled, the vacuum tube is removed from the open end 24 of the tube holder 20. If desired, another vacuum tube can be inserted so that additional fluid can be collected. After the operator has collected sufficient fluid from the patient and the last vacuum tube 80 has been removed, the needle is withdrawn from the patient. The operator then depresses the actuation button 50 to retract the needle 30 into housing 41. Coil spring 38 propels the double-ended needle 30 rearwardly into barrel 41 so that the tip 32 of the needle 30 is enclosed within the housing 41 of the fluid collection device 10. Fluid collection device 10 can then be safely discarded, or the needle assembly 40 with the retracted needle 30 can be carefully removed from the tube holder 20 and discarded, so that the tube holder can be reused with a new needle assembly.

Referring now to FIGS. 5, 6A and 6B, an alternative embodiment is illustrated. The device 10' is similar to the device illustrated in FIGS. 1-4 and described above. Elements of the device that are similar to the corresponding elements of the embodiment discussed above are designated with the same reference numbers with the addition of a thereto.

The device 10' includes an actuation button 50' for actuating needle retraction. Actuation button 50' is shown prior to actuation in FIG. 6A, and subsequent to actuation in FIG. 6B. Button 50' includes an arcuate button portion and two side members 52' and 54' and is preferably circumferentially aligned with the bevel of needle end 32 as in the device illustrated in FIG. 1. Actuation button 50' is positioned in transverse slot 49' and includes a bottom member 53' connecting the bottom ends of side members 52' and 54' and upon which flange 62 of needle tube 60 directly bears to hold double-ended needle 30 in its extended-for-use position. Indentations 56' in side members 52' and 54' contact the interior of barrel 41' forming detents to hold actuation button 50' in the unactuated position as shown in FIG. 6A.

When actuation button 50' is depressed, button 50' moves transversely in transverse slot 49' to the position shown in FIG. 6B, a position in which it may be held by indentations 58' engaging a lip on the interior of barrel 41'. With button 50' in actuated position, bottom member 53' is displaced outwardly from flange 62 of needle tube 60, thereby disengaging needle tube 60 and allowing needle tube 60 and double-ended needle 30 affixed thereto to move rearward under the urging of coil spring 38. Needle tube 60 and double-ended needle 30 are captured and retained in the retracted needle position within barrel 41' in like manner to that described above in relation to FIGS. 1-4.

Figure 8A:
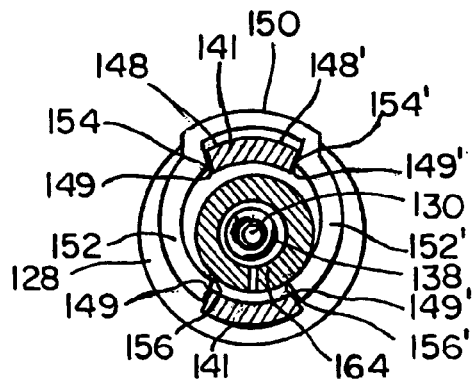
FIG. 8A is a cross-sectional view of the device shown in FIG. 7 taken along the line 8-8.
Figure 8B:
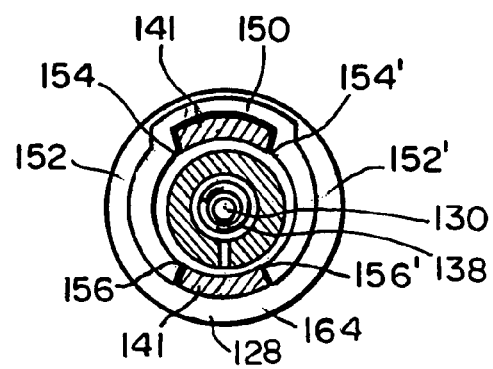
FIG. 8B is a cross-sectional view of the device illustrated in FIG. 8A, showing the device after actuation of needle retraction.
Figure 9:
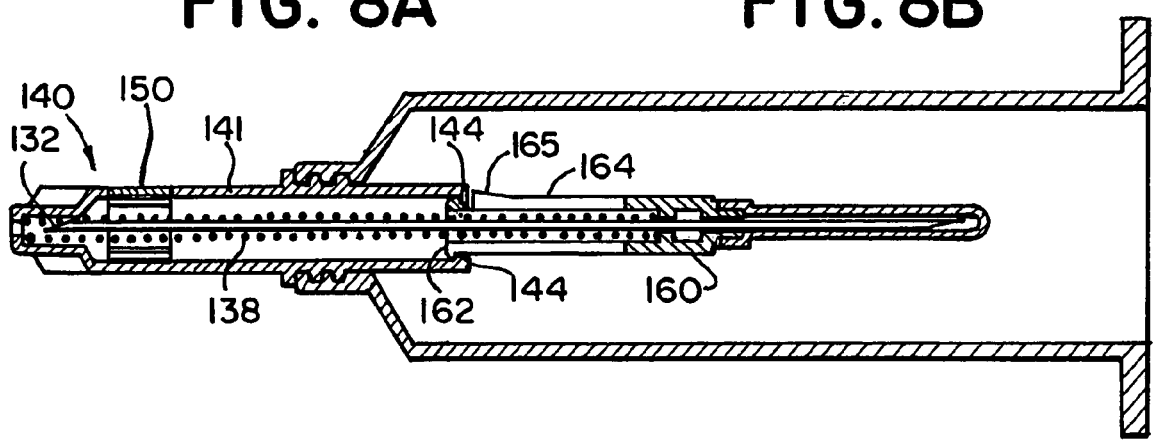
FIG. 9 is a sectional diagram of the device shown in FIG. 7, showing the device after actuation of needle retraction.

Referring now to FIGS. 7-9, another alternative embodiment is shown. The device 110 is similar to the device illustrated in FIGS. 1-6B and described above. Elements of the device that are similar to the corresponding elements of the embodiments described above are identified with a similar reference number with the addition of 100's thereto.

The device 110 includes a tube holder 120 adapted for receiving a vacuum tube fluid collection container and a needle assembly 140. Double-ended needle 130 has a sharpened front needle end 132 for piercing a patient and a sharpened rear needle end 134 for piercing a seal on the fluid collection container. The needle assembly 140 is removably connected to the front of the tubeholder 120. Needle assembly 140 includes a barrel housing 141 through which double-ended needle 130 passes.

A needle tube 160 is slidably mounted within barrel 141 of needle assembly 140 and has at its rearward end a flexible rubber or plastic boot 168 for maintaining the cleanliness and sterility of needle end 134. At its forward end needle tube 160 has a flange 162 in releasable engagement with actuation button 150 for holding needle tube 160, and thus double-ended needle 130, in the forward or needle-extended position. Button 150 is preferably circumferentially aligned with the bevel of needle end 132, as shown in FIG. 7.

Needle tube 160 further includes a flexible member 164 having an a protrusion 165 projecting outwardly therefrom. Flexible member 164 may be formed, for example, by a "U"-shaped slot in needle tube 160 with the open end of the "U" toward the rearward portion of needle tube 160. Coil spring 138 is compressed when the needle 130 is in the needle-extended position bearing against the forward portion of needle assembly 140 and against the bottom of the bore 166 of needle tube 160 for urging needle tube 160 and double-ended needle 130 affixed thereto in a rearward direction. Barrel 141 of needle assembly 140 includes external transverse grooves 149, 149' into which arcuate sides 152, 152' of actuation button 150 are inserted. As so assembled, button 150 engages flange 162 of needle tube 160 for holding needle tube 160 and needle 130 in the needle-extended position.

FIGS. 8A and 8B are cross-sectional views of the embodiment of FIG. 7 showing actuation button 150 in the latched and released positions, respectively. The actuating button includes an arcuate button portion 150 for being depressed and two arcuate side members 152 and 152' joined therewith to form a horseshoe-shaped piece that straddles the external transverse grooves 149, 149' of barrel 141. Button 150 is molded with the arcuate sides 152 and 152' closer together than the dimensions between the exterior groove 149, 149' of barrel 141 so that when inserted over the barrel 141 arcuate sides 152 and 152' press inward and hold button 150 on barrel 141 with shoulders or edges 154, 154' bearing against shoulders 148, 148', respectively, of barrel 141. In this latched configuration with the double-ended needle 130 in its needle-extended position, shoulders 156 and 156' of arcuate sides 152, 152', respectively, engage flange 162 of needle tube 160, i.e. are in releasable engagement with flange 162, thereby holding needle tube 160 and double-ended needle 130 in the needle-extended position.

Depressing the actuation button 150 releases the needle tube 160 and needle 130, so that the spring 138 retracts the needle. When actuation button 150 is pushed to actuate needle retraction, button 150 moves downwardly onto barrel 141 along grooves 149, 149' into a depressed or actuated position. After depressing the button 150, arcuate sides 152 and 152' are positioned so as to be substantially concentric with needle tube 160 so that shoulders 156, 156' are clear of flange 162 of needle tube 160, thereby allowing needle tube 160 to be propelled rearwardly under the urging of coil spring 138. The protrusion 165 on the flexible member 164 is tapered. Therefore, during retraction the flexible member 164 biases inwardly when the protrusion engages 165 flange 144 so that the protrusion clears the flange, allowing the needle tube to continue to retract rearwardly.

When needle tube 160 and double-ended needle 130 reach the needle-retracted position, as shown in FIG. 9, flange 162 of needle tube 160 comes to bear against inwardly projecting flange or lip 144 of barrel 141 which stops the rearward motion of needle tube 160. Protrusion 165 engages the rearward edge of flange 144, thereby preventing re-extension of double-ended needle 130. Accordingly, needle tube 160 and double-ended needle 130 are captured, i.e. are positively retained, in the needle-retracted position by the engagement of flange 162, the same engaging feature that held double-ended needle 130 in the needle-extended position, with engaging feature 165 of flexible member 164 and flange 144 of needle assembly 140.

Figure 10:
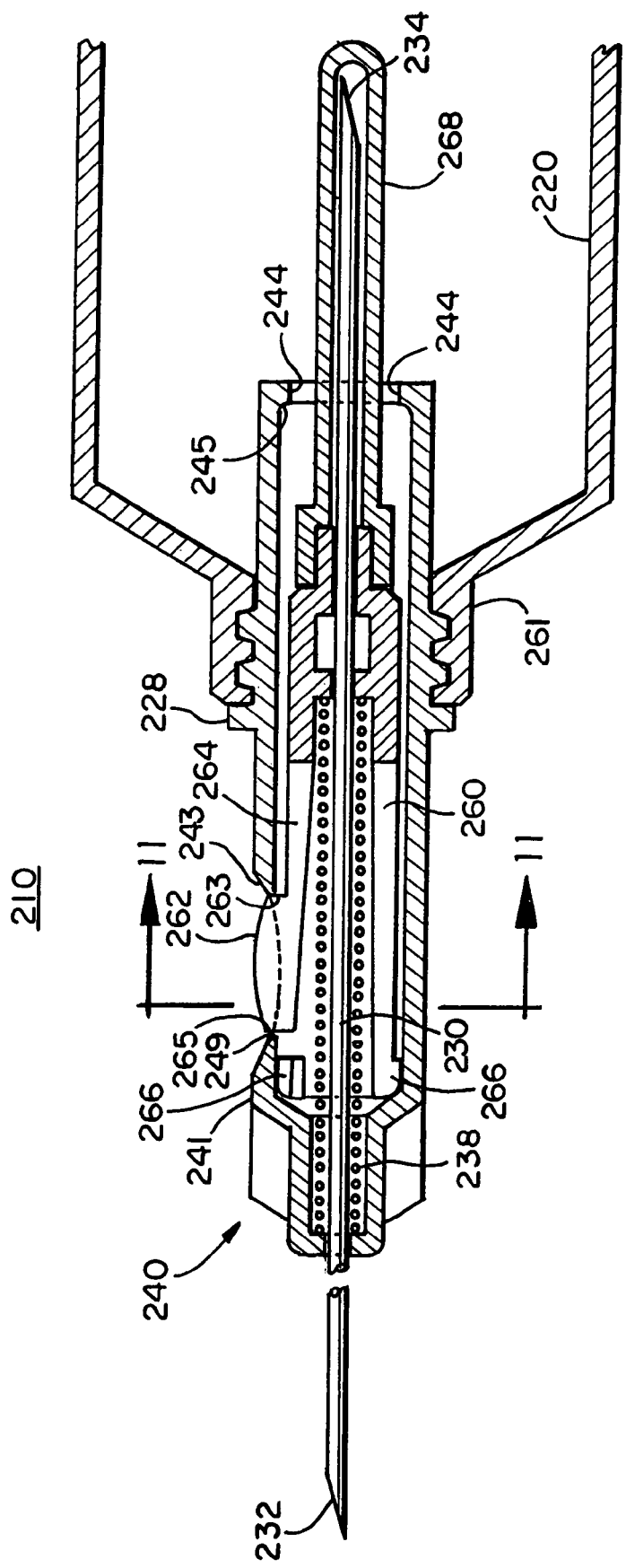
FIG. 10 is a sectional view of the preferred embodiment of a fluid transfer device having a retractable needle.

Referring now to FIGS. 10-12, yet another alternate embodiment is illustrated. The device 210 is the preferred embodiment and is similar to the embodiments illustrated in FIGS. 1-9 and discussed above. Accordingly, elements in the device 210 that are similar to the elements in the embodiments discussed above are identified with similar reference numbers with the addition of 200's thereto.

The device 210 includes a needle assembly 240 threadedly connected to a tube holder 220. The needle assembly 240 includes a housing barrel 241 in which double-ended needle 230 is slidably mounted and operable between the forward or needle extended position in which front needle end 232 extends from housing barrel 241 and a rearward or needle retracted position in which front needle end 232 is enclosed by barrel 241. Double-ended needle 230 is fixedly mounted in needle tube 260 such as by adhesive applied through bonding port 261, or alternatively by a press fit or by insert molding. A coil spring 238 biases needle tube 260 and double-ended needle 230 towards the rearward retracted-needle position. In the needle-extended position, double-ended needle 230 is prevented from being propelled into the rearward or needle-retracted position by coil spring 238 because an engaging member 262 of needle tube 260 is in releasable engagement with an engaging feature 243 of barrel 241. As shown in FIG. 10, the engaging feature 262 of the flexible member is a detent, or button, and engaging feature 243 is the rim of a hole 249 in barrel 241. Button 262 has a shoulder at its rearward edge 263 which engages the rim 243 of the hole 249 in barrel 241. Flexible member 264 is radially deformable, so that button 262 is radially displaceable with respect to housing barrel 241 and engaging feature 243 thereof. Button 262 is preferably circumferentially aligned with the bevel of needle end 232 as shown in FIG. 10.

To actuate retraction of needle 230, actuation button 262 is depressed, displacing the button into the interior of barrel 241 and thereby disengaging the engaging feature 263 of the needle 230 and needle tube 260 from the engaging feature 243 of barrel 241. Thus released, coil spring 238 propels needle tube 260 and needle 230 affixed therein rearward to the needle-retracted position. Button 262 is preferably recessed below the surface of barrel 241 so as to reduce the likelihood of unintentional retraction of needle 230.

FIGS. 11A and 11B are cross-sectional views of the embodiment of FIG. 10 showing the engaging member and actuation button 262 in its latched and unlatched positions, respectively. The circular cross-section of needle tube 260 is positioned within the circular interior of barrel 241 which includes a hole 249 therein. Flexible member 264 is a resilient arm biased radially outwardly so that button 262 is biased into engagement with the rim 243 of the hole in the barrel 241 in the latched position. The particular position shown in FIG. 11A is the substantially relaxed position of flexible member 264. In this position, the rearward end 263 of button 262 is engaged with the rim 243 of barrel 241. Depressing button 262 displaces the button out of engagement with hole 249, so as to be fully within the interior of barrel 241, as shown in FIG. 11B. In this way, depressing button 262 disengages shoulder 263 from the rim 243 of the hole 249 in the barrel 241 to permit needle 230 and needle tube 260 to move rearwardly under the urging of spring 238 until needle 230 comes to rest in its needle-retracted position as described below.

In FIG. 12, double-ended needle 230 is in the needle-retracted position with front needle end 232 retracted within the housing barrel 241. Double-ended needle 230 fixed in needle tube 260 is held in the retracted needle position by the engagement of button 262 at its forward end 265 with an interior circumferential flange or lip 244 on barrel 241. Thus engaged, needle 230 is precluded from being easily re-extended or returned to the needle-extended position.

In traveling to the retracted-needle position under the urging of coil spring 238, button 262 engages the beveled forward shoulder 245 of lip 244 which flexes arm 264 radially inwardly thereby displacing the button 262 radially inwardly, so that button 262 may pass through the restrictive opening formed by lip 244. When button 262 has passed rearwardly beyond lip 244, the flexed arm 264 reflexes radially outwardly thereby displacing button 262 radially outwardly so that forward end 265 engages the rearward shoulder of lip 244. In this way, the engagement between the button 262 and the lip operate as a stop preventing the needle from being re-extended after retraction. The rearward travel of needle tube 260 is limited or stopped by the circumferential flange 266 engaging the forward shoulder 245 of lip 244. As a result, needle tube 260 and needle 230 contained therein are retained in the retracted-needle position by flange 266 and button 262 being in engagement with lip 244 of housing barrel 241.

For assembly of needle tube 260 into barrel 241, barrel 241 could be fabricated in two sections that are adhesively attached to each other following insertion of needle tube 260 therein. Alternatively, needle tube 260 can be constructed with gaps in the circumferential flange 263 and barrel 241 can be fabricated with corresponding gaps in flange 244 so that when held in a predetermined orientation, the gaps in flange 263 align with the segments of lip 244 and the gaps in lip 244 align with the segments in flange 263 so that needle tube 260 slips inside barrel 241. Alternatively, and preferably, the forward edge of the flange 266 on the needle tube is rounded and the rearward edge of the flange is generally square. During assembly the needle tube 260 is force fit into barrel 241, resiliently compressing the flange 266 when the flange engages the restricted flange 244 of barrel 241. The rounded edge of flange 266 facilitates compressing the needle tube flange 266. After the needle tube flange 266 is axially displaced forward of the barrel flange 241 the needle tube flange resiliently rebounds radially outwardly so that the needle tube flange is larger in diameter then the contracted opening formed by barrel flange 241.

Tube holder 220, rear needle end 244 and flexible boot 268 are similar to those described above in relation to FIGS. 1 and 7, for example.

In any of the preceding embodiments, doubled-ended needle 30, 130, 230 is preferably made of stainless steel, housing barrel 41, 141, 241 is preferably made of polypropylene or polycarbonate, needle tube 60, 160, 260 is preferably made of polycarbonate or acrylic, vacuum tube holder 20, 120, 220 is preferably made of polypropylene or polyethylene, flexible boot 68, 168, 268 is preferable made of an elastomeric material, such as isoprene rubber or silicone or santoprene synthetic rubber, and actuation button 50, 150 is preferably made of polycarbonate.

Accordingly, a fluid collection device 10, 110, 210 has been described which is operable with a fluid collection container 80. The fluid collection device includes a housing 41, 141, 241 and a double-ended needle 30, 130, 230 having first and second needle ends 32, 132, 232, 34, 134, 234 that is operable between an extended needle position in which the first needle end of the double-ended needle 32, 132, 232 projects from the housing 41, 141, 241 and a retracted needle position in which the first needle end 32, 132, 232 is enclosed within the housing, 41, 141, 241. The double-ended needle 30, 130, 230 further includes a first engaging member 62, 162, 262 on its outer surface and is biased towards the retracted needle position by a biasing element such as a coil spring 38, 138, 238. A second engaging member 42, 53', 150, 243 is in releasable engagement with the first engaging feature 62, 162, 262 associated with the double-ended needle 30, 130, 230 when the needle 30, 130, 230 is in the extended needle position. One of the first and second engaging members 62, 162, 262, 42, 53', 150, 243 is moveable with respect to the other of the first and second engaging members 62, 162, 262, 42, 53', 150, 243 for providing the releasable engagement, thereby to operate the double-ended 30, 130, 230 needle to move from the extended needle position to the retracted needle position. An engaging feature 44, 46, 48, 144, 164, 165, 244 on the housing 41, 141, 241 engages the first engaging member 62, 162, 262 of the double-ended needle 30, 130, 230 when the double-ended needle 30, 130, 230 is in its retracted needle position, whereby the double-ended needle 30, 130, 230 is retained in the retracted needle position within the housing 41, 141, 241.

Additionally, a fluid collection device 10, 110 has been described which is operable with a fluid collection container 80. The fluid collection device includes a housing 41, 141 and a double-ended needle 30, 130 having first and second needle ends 32, 132, 34, 134 that is operable between an extended needle position in which the first needle end of the double-ended needle 32, 132 projects from the housing 41, 141 and a retracted needle position in which the first needle end 32, 132 is enclosed within the housing, 41, 141. The double-ended needle 30, 130 further includes an engaging feature 62, 162 on its outer surface and is biased towards the retracted needle position by a biasing element such as a coil spring 38, 138. An engaging member 42, 53', 150 which is moveable with respect to the double-ended needle 30, 130 releasably engages the engaging feature 62, 162 of the double-ended needle 30, 130 when the needle is in the extended needle position and is moveable to operate the double-ended needle to move from the extended needle position to the retracted needle position. The housing 41, 141 further includes means 44, 46, 48, 144, 164, 165 for engaging the engaging feature 62, 162 of the double-ended needle 30, 130 when the double-ended needle 30, 130 is in its retracted needle position, whereby the double-ended needle 30, 130 is retained in the retracted needle position within the housing 41, 141.

Figures 13A, 13B:
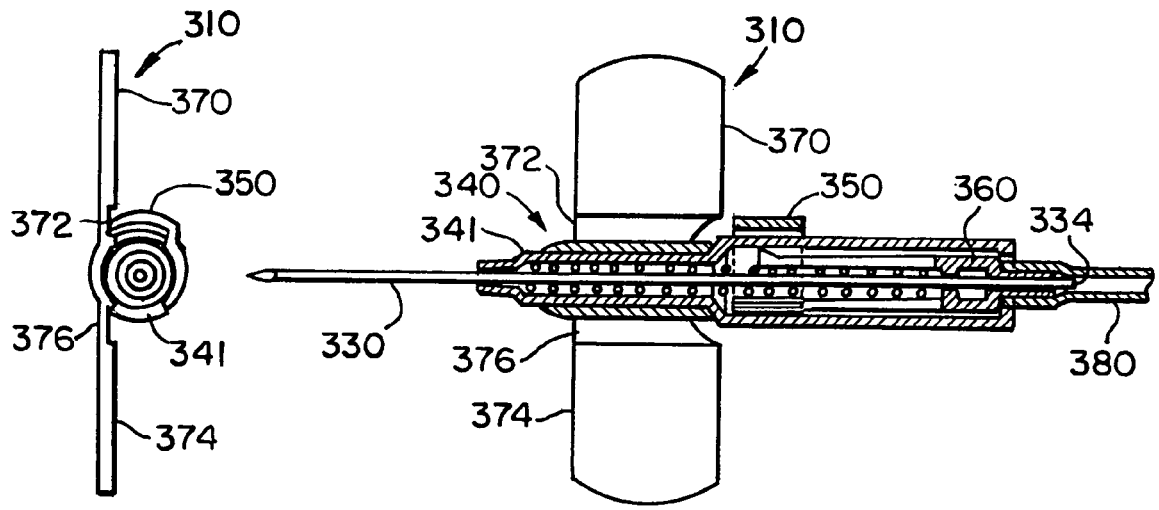
FIG. 13A is a sectional view of a fluid transfer device having wings.
FIG. 13B is a front end view of the device shown in FIG. 13A.

Yet another alternative embodiment is illustrated in FIGS. 13A and 13B. The device 310 includes a pair of wings 370, 374 and is similar to the device illustrated in FIGS. 7-9, and discussed above. Accordingly, elements in the device 310 that are similar to elements of the device 110 illustrated in FIGS. 7-9 are identified with like reference numbers with the addition of 300's thereto.

Butterfly wings 370 and 374 extend outwardly from barrel 341 and are generally planar surfaces suitable for being taped to a patient's body for securing the fluid collection device 310 in place after needle 330 has been inserted into the patient. Wing 370 includes a thinned narrowed portion 372 and wing 374 includes a thinned narrowed portion 376 for providing additional flexibility between wings 370 and 374 and the barrel 341 of needle assembly 340 for the comfort of the patient. The thinned portions 372, 376 act as living hinges about which the wings 370, 374 are pivotable. Wings 370 and 374 are preferably in substantially the same plane and are affixed to the needle assembly 340 at a location tangential to its external surface. Preferably wings 370 and 374 are molded integrally with barrel 341. Preferably rearward needle end 334 is blunt and extends from a rearward cylindrical fitting 367 of needle tube 360 that is adapted for connection to a fluid conducting device such as a plastic tube 380 which extends over and is retained on the fitting 367 of needle tube 360 by friction or by an adhesive. Alternatively, the fitting 367 of needle tube 380 may have an adapter suitable for receiving a female luer fitting or other standard medical device fitting at the end of the tube 380. Alternatively, blunt needle end 334 can be adapted for being in fluid communication with a vial, the contents of which are to be injected into a patient through needle 330. These features may be employed with any of the embodiments described herein.

Yet another alternative embodiment is illustrated in FIGS. 14A-16. The device 410 incorporates wings 470, 474 and is similar to the embodiment illustrated in FIGS. 10-12. Accordingly, elements of the device 410 that are similar to the elements of the device 410 illustrated in FIGS. 10-12 are identified with similar reference numbers with the addition of 400's thereto. For example, the reference numeral 444 in FIGS. 14B and 15 identifies a lip of a barrel 441 that is similar to the lip 244 of housing barrel 241 illustrated in FIGS. 10 and 12, and the reference numeral 462 in FIGS. 14B and 15 identifies an actuation button that is similar to the actuation button 262 illustrated in FIGS. 10-12.

Figures 14A, 14B:
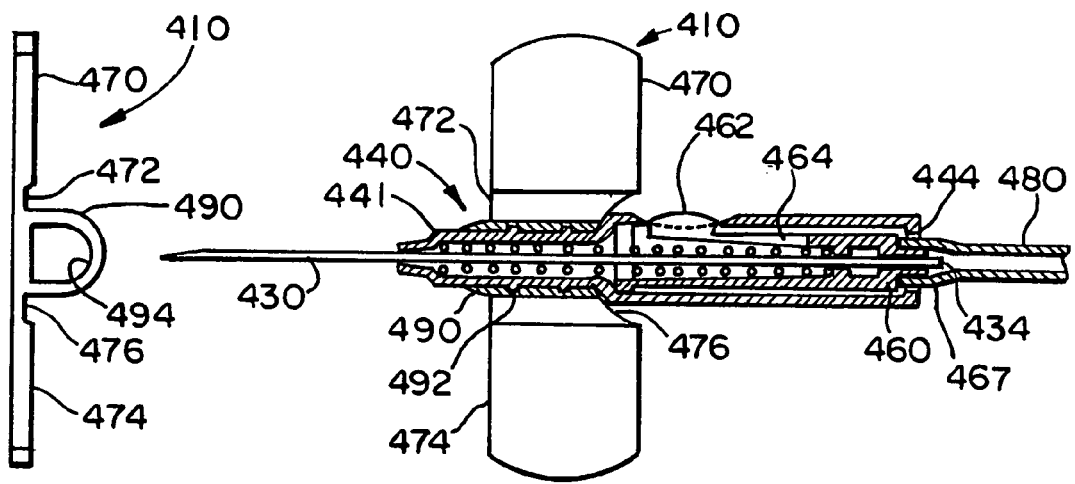
FIG. 14A is a sectional view of an alternate embodiment of a fluid transfer device having wings.
FIG. 14B is a front end view of the wings of the device shown in FIG. 14A.
Figure 22:
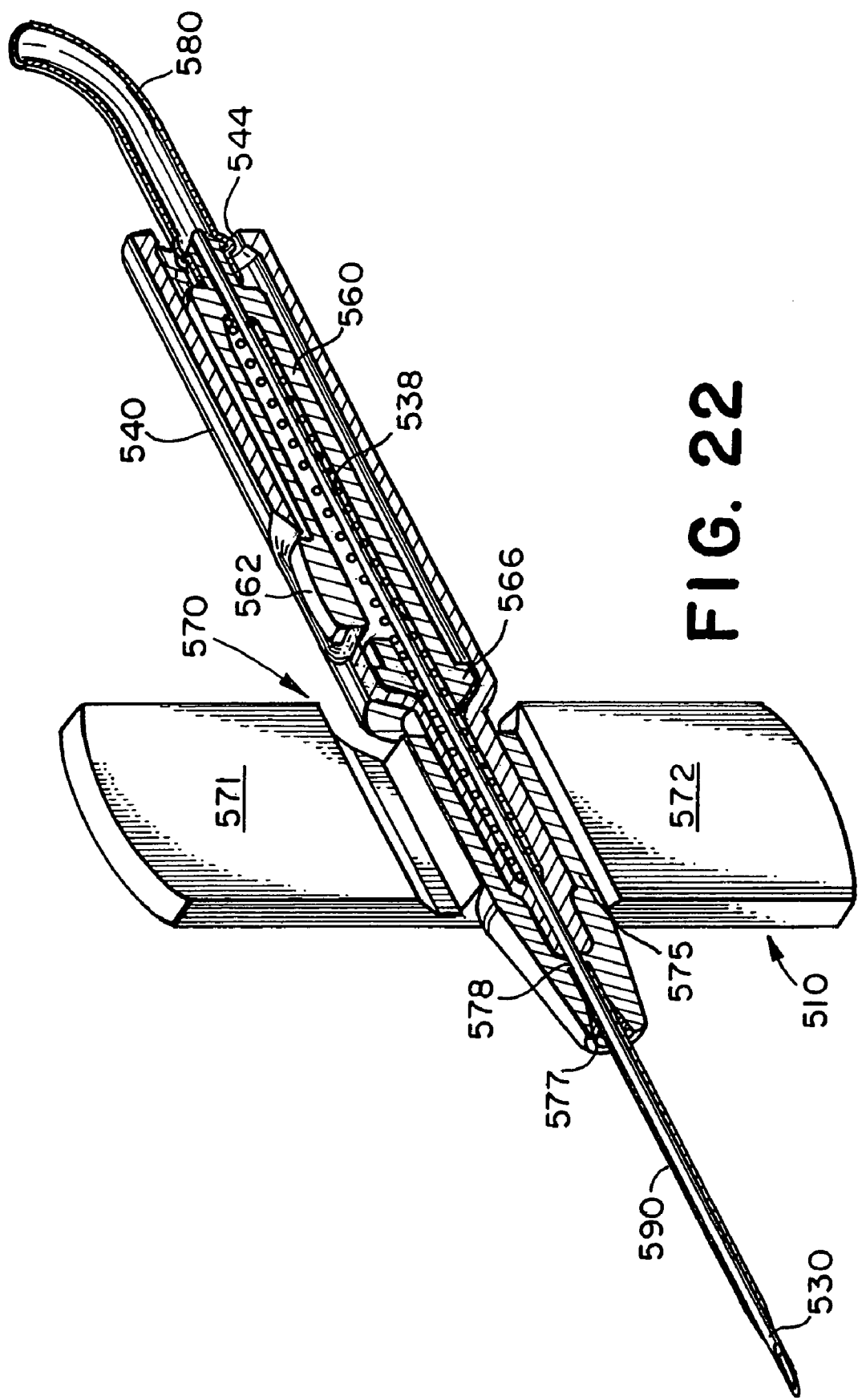
FIG. 22 is an enlarged fragmentary perspective view in section of the device illustrated in FIG. 17.
Figure 23:
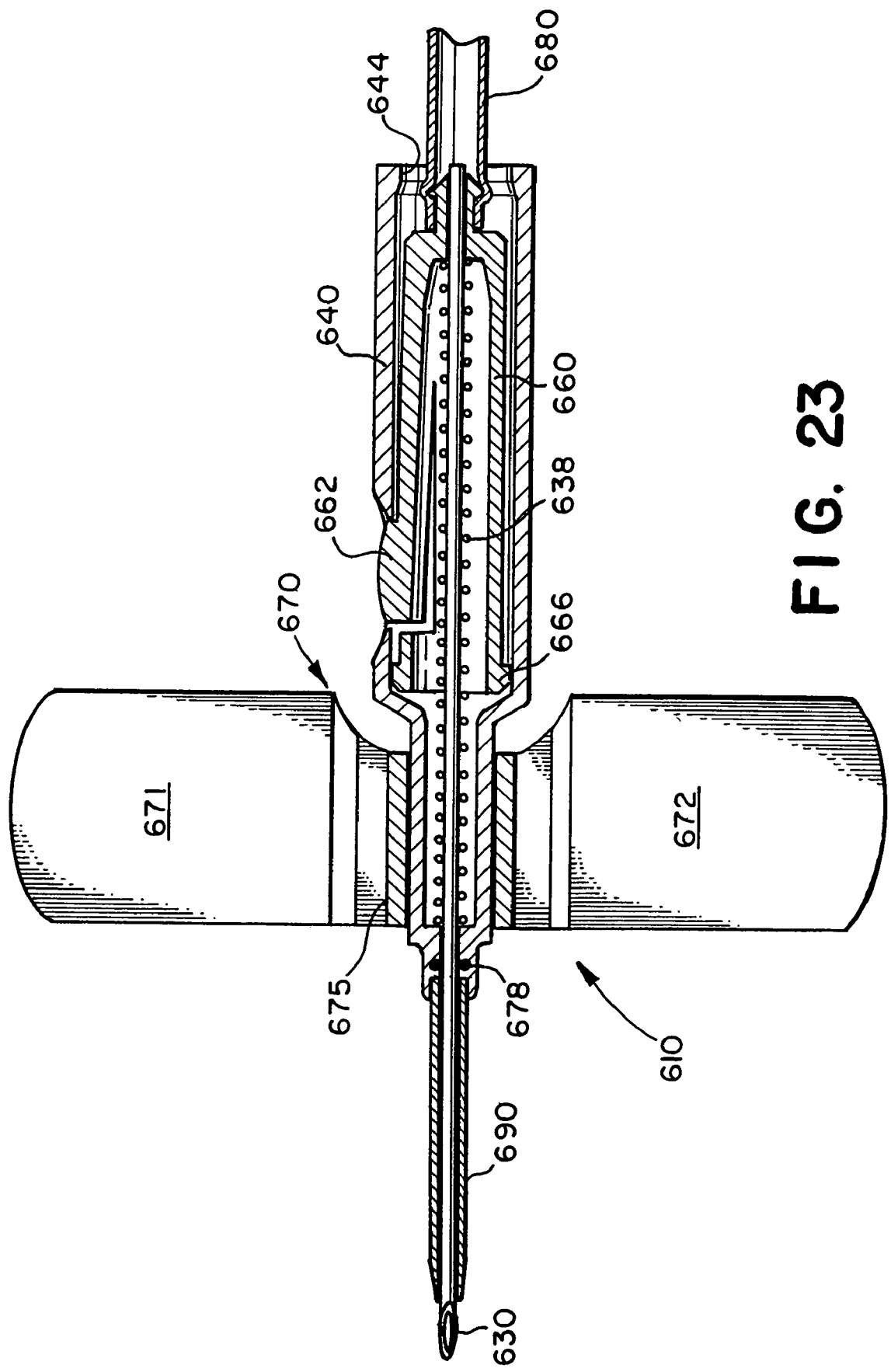
FIG. 23 is a cross-sectional view of an alternate fluid transfer device with a fixed catheter.
Figure 24:
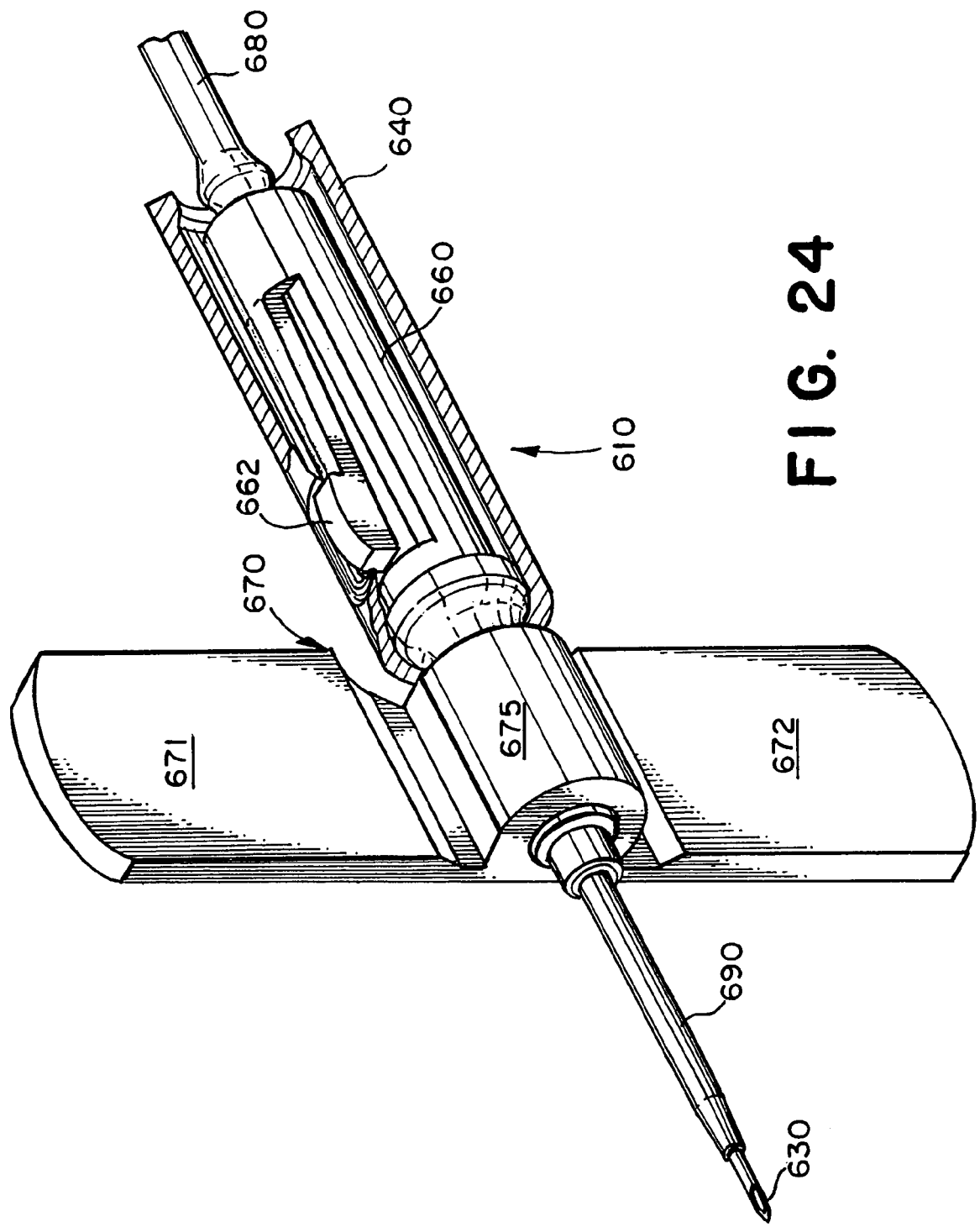
FIG. 24 is a perspective view of the device illustrated in FIG. 23.
Figure 25:
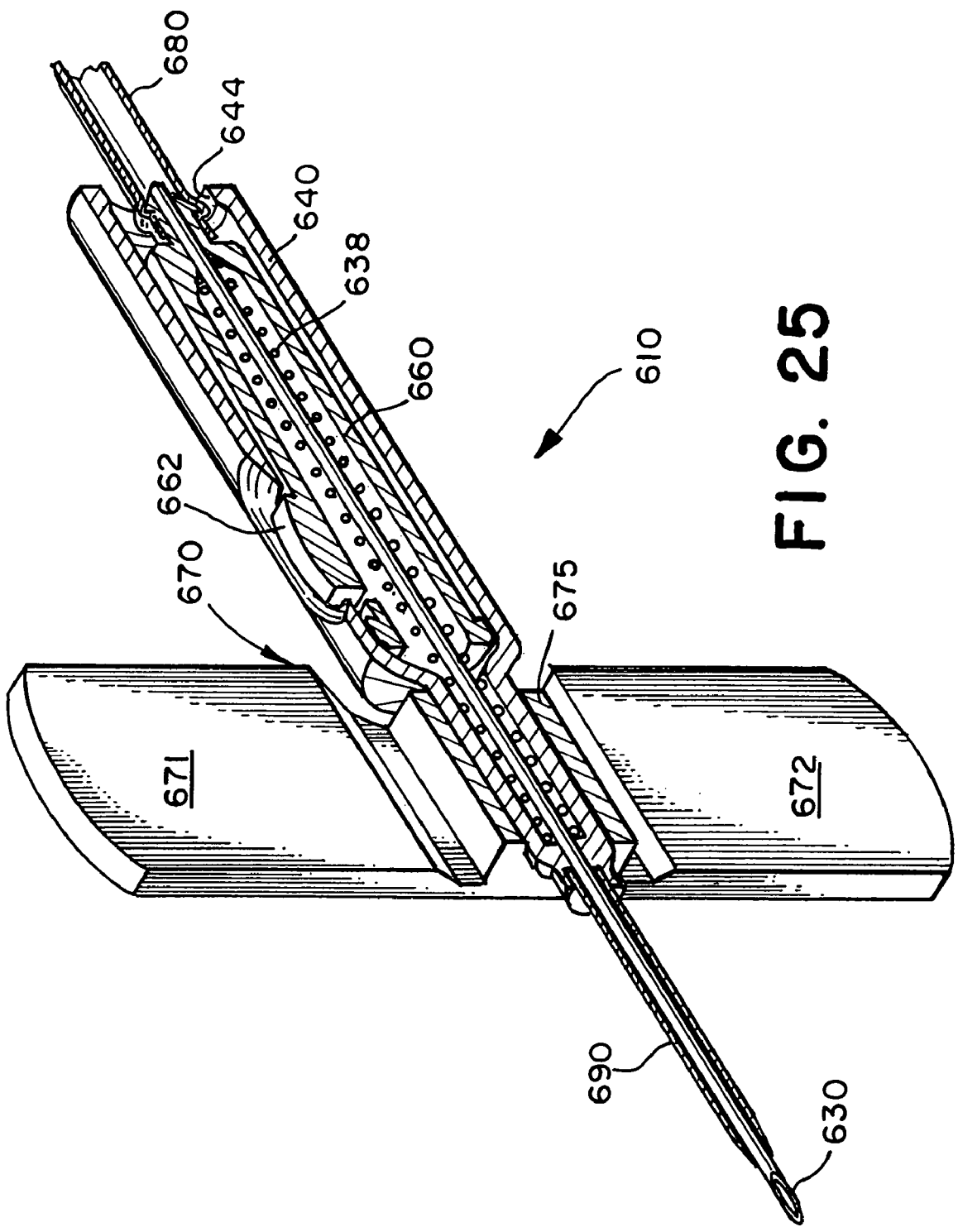
FIG. 25 is a perspective view in section of the device illustrated in FIG. 23.

Butterfly wings 470 and 474 extend outwardly from barrel 441 and are generally planar surfaces, suitable for being taped to a patient's body after the needle 430 has been inserted into the patient. Wings 470 and 474 include thinned narrowed portions 472 and 476, respectively, for providing additional flexibility between wings 470 and 474 and the barrel 441. The thinned portions 472, 476 operate as living hinges about which the wings 420, 474 pivot. Wings 470 and 474 are preferably in substantially the same plane and are affixed to the needle assembly 440 at a location tangential to its external surface by inserting barrel 441 into passage 494 of "D"-shaped body 490. The body 490 is held in place by corresponding ridges and grooves 492 in barrel 441 and loop 490, respectively. Alternatively, the body 490 can be connected to the barrel 441 by adhesive or friction fit. In FIGS. 14A and 14B, as in FIGS. 13A and 13B, rearward needle end 434 is blunt and extends from a rearward cylindrical fitting 467 of needle tube 460 that is adapted for connection to a fluid conducting device such as a plastic tube 480.

In FIG. 15, the needle 430 is fixed to the needle tube 460 by adhesive inserted axially at end of needle tube 460. Alternatively, needle 430 could be attached to needle tube 260 by friction fit or by being insert molded.

In FIG. 16, the device 410 is shown in combination with a length of vinyl tubing 480 and a tube holder 420. The first end of the tubing 480 is connected at one end to the fitting 467 on the needle tube 460. Preferably, a female luer fitting 482 is attached to the second end of the tubing 480. Female luer fitting 482 cooperates with a male luer fitting 484 that threadedly engages the tube holder 420. A rear needle 486 for puncturing the seal on a vacuum tube is connected to the male luer fitting 484. In this way, the rear needle is in fluid communication with needle 430.

Referring now to FIGS. 17-22, an alternate fluid transfer device 510 is illustrated. The device 510 incorporates a fixed catheter 590 attached to the front end of the device. The device 510 is operable to either withdraw fluid from a patient or to inject fluid into the patient.

The device 510 includes a retractable needle 530 releasably retained in an extended position projecting forwardly from a barrel 540 by a needle retainer. In the present instance, a needle tube 560 attached to the rearward end of the needle 530 includes an arm that extends radially outwardly from the needle tube. A button 562 integrally formed on the end of the arm engages an aperture in the side of the barrel 540 to retain the needle tube 560 and the attached needle 530 in the extended position. Depressing the button 562 disengages the button from the aperture, releasing the needle tube, and a spring 538 propels the needle 530 rearwardly into the housing. The spring 538 is a coil spring disposed about the needle 530. In the present instance the spring 538 extends between the forward end of the tip of the barrel 540 and the rearward end of the needle tube 560.

The forward portion of the barrel 540 forms a reduced diameter tip to which a wing assembly 570 is attached. The wing assembly 570 is made of a resilient material such as polyurethane, PVC or a thermoplastic elastomer such as SANTOPRENE which is manufactured by Advanced Elastomer Systems. The wing assembly 570 includes a body 575 and a pair of generally parallel wings extending transverse the body. The wing body 575 is hollow having a bore that cooperates with the exterior of tip of the barrel 540. An annular protrusion 578 projects inwardly into the bore of the wing body 575. The protrusion 578 is located forward of the forward end of the barrel tip, and acts as a seal as is discussed further below.

The forward portion of the wing body 575 forms a reduced diameter tip having a recess or socket 577 for receiving a flexible catheter 590. The catheter 590 is permanently fixed within the socket 577 by epoxy.

In the extended position, the needle 530 extends forwardly from the barrel 540 through the catheter 590 so that the sharpened tip of the needle projects from the forward end of the catheter.

The device operates as follows. The sharpened tip is inserted into a patients vein, thereby inserting the catheter 590 into the patient's vein. Once the needle is inserted, the button 562 is depressed to retract the needle 530 into the housing. As in the previously described embodiments, the device 510 includes forward and rearward needle stops. The rearward end of the barrel 540 includes an internal flange 544 that cooperates with an external flange 566 on the needle tube 560 to prevent the spring from propelling the needle out of the barrel. The internal flange 544 on the barrel also cooperates with the forward end of the button 562 to prevent the needle 530 from being re-extended after retraction.

After needle retraction, preferably a seal is provided to provide a fluid-tight seal between the catheter 590 and the needle 530. In the present instance, in the retracted position, the internal protrusion of the wing 578 engages the needle 530 thereby providing a seal between the needle and the catheter. As can be seen in FIG. 20, the seal 578 also engages the needle when the needle is in the extended position, so that the seal forms a sliding seal with the needle, maintaining a fluid-tight seal before, during and after retraction.

After the needle is retracted, the wings 571, 572 are then taped to the patient to retain the device 510 in place. Fluid is then either withdrawn from the patient exiting rearwardly into the flexible tube 580, or fluid is injected into the patient from the flexible tube.

In FIGS. 23-26 an alternate catheter bearing fluid transfer device 610 is illustrated. The alternate catheter bearing device is configured similarly to the previously described embodiment and functions similarly. Therefore, elements that are similar to the elements in the previously described catheter device 510 are designated with similar reference numbers with the addition of 600's thereto.

The device 610 includes a retractable needle projecting forwardly from a barrel 640 and through a catheter 690 attached to the forward end of the barrel. In the present embodiment, the body 675 of the wing assembly 670 is foreshortened so that the forward end of the tip of the barrel 640 projects from the forward end of the wing body 675. The catheter is 690 bonded to the tip of the barrel. As shown in FIG. 20, a separate seal 678 is disposed in the interior of the tip of the barrel 640. The seal 678 is an annular seal such as an o-ring, and it provides a fluid-tight seal between the needle 630 and the catheter 690 after the needle is retracted. The needle retainer and actuation of retraction is similar to retention and retraction described above, including the forward and rearward needle stops.

While the present invention has been described in terms of the foregoing exemplary embodiments, variations within the scope and spirit of the present invention as defined by the claims following will be apparent to those skilled in the art. For example, the protruding engaging features such as flange 62, 162 of needle tube 60, 160 could be replaced by an indented engaging feature, for example, by a hole or a groove, with corresponding changes being made with that member with which it engages, for example, groove 48 becoming a flange or a tab or boss to fit into a respective hole or groove that replaces flange 62, 162.

Variations in the shape and form of needle tube 60, 160, 260 which serves as a carrier for needle 30, 130, 230 may also be made. For ease of assembly, it may advantageous to provide a symmetry to needle tube 60 so that it has a section of a flange 62 and another section of a flange 64 substantially 180° apart whereby it may be installed in barrel 41 of needle assembly 40 in either orientation. Similarly, needle tube 160 could have two flexible arms 164 with engaging features 165 thereon spaced 180° apart on needle tube 160 which would provide a double gripping action when needle tube 160 is captured in the needle retracted position engaging stopping flange 144. Similarly, flexible arm 164 could have an indented engaging feature such as a hole or a groove rather than a projecting engaging feature 165, that would engage a protruding engaging feature engaging a flange or boss that replaces flange 144 on barrel 141.

While the foregoing exemplary embodiments have been described with respect to a double-ended needle 30, 130 mounted through a needle tube 60, 160, it is equally satisfactory that double-ended needle 30, 130 include engaging features on its external surfaces such as a flange or ridge or shoulder, whether formed integrally or bonded thereon, to engage features on housing 41, 141.

For insertion of needle tube 60, 160 into needle assembly 40, 140, needle tube 60, 160 may be constructed with sufficient flexibility so that engaging feature 62 may be flexed to allow insertion into barrel 41, 141, or the engaging features on needle tube 60, 160 and on barrel 41, 141 may be segmented with a correspondence between the gaps in one and the features of the other to allow, in a particular orientation, insertion of needle tube 60, 160 into barrel 40, 141.

Referring now to FIGS. 27-32, yet another embodiment of a fluid collection device 810 is illustrated. The device 810 includes a front needle 830 projecting forwardly from a barrel 820. The front needle 830 is inserted into a patient to collect fluids, such as blood from the patient. After use, the front needle 830 is retracted rearwardly so that the sharpened tip of the front needle is enclosed within the device 810.

The fluid collection device 810 includes a hollow generally cylindric barrel or housing 820. The rearward end of the barrel 824 is generally open forming a socket for receiving a fluid collection container, such as a vacuum tube 880. A circumferential flange 822 adjacent the open end 824 provides a finger gripping area for the user. The forward end 826 of the barrel 820 is generally closed having a reduced diameter opening. Preferably, the opening at the forward end 826 has internal threads 827 that threadedly engage a needle assembly 840 as is discussed further below.

The needle assembly 840 releasably retains the front needle 830 in an extended position projecting forwardly from the barrel 820. The needle assembly 840 includes the front needle 830 and a rear needle 835. A cylindrical conduit 860 extends between the front needle 830 and the rear needle 835 so that the front needle and the rear needle are in fluid communication. As shown in FIG. 27, preferably the rearward end of the conduit 860 is generally closed having a reduced diameter opening through which the rear needle 835 extends. Preferably the rear needle 835 is fixedly retained in the rearward opening of the conduit 860. The needle assembly 840 further includes a generally cylindrical tip 842 connected to the forward end of the conduit 860. The rearward end of the tip 842 is generally open, and the forward end of the tip 842 is generally closed, forming a reduced diameter opening through which the front needle 830 extends. As can be seen best in FIG. 29, the forward end of the conduit 860 is inserted into the rearward end of the cylindrical tip 842 so that the conduit engages the internal bore of the cylindrical tip.

Figure 30:
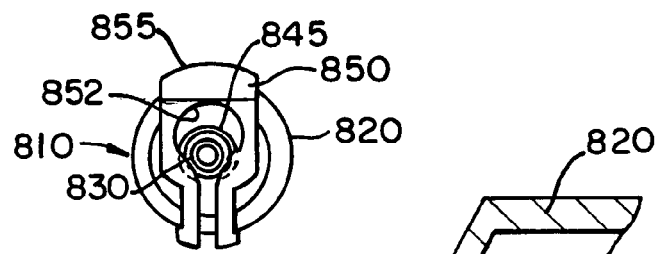
FIG. 30 is a cross-sectional view of the fluid collection device illustrated in FIG. 29, taken along line 30-30.
Figure 29:
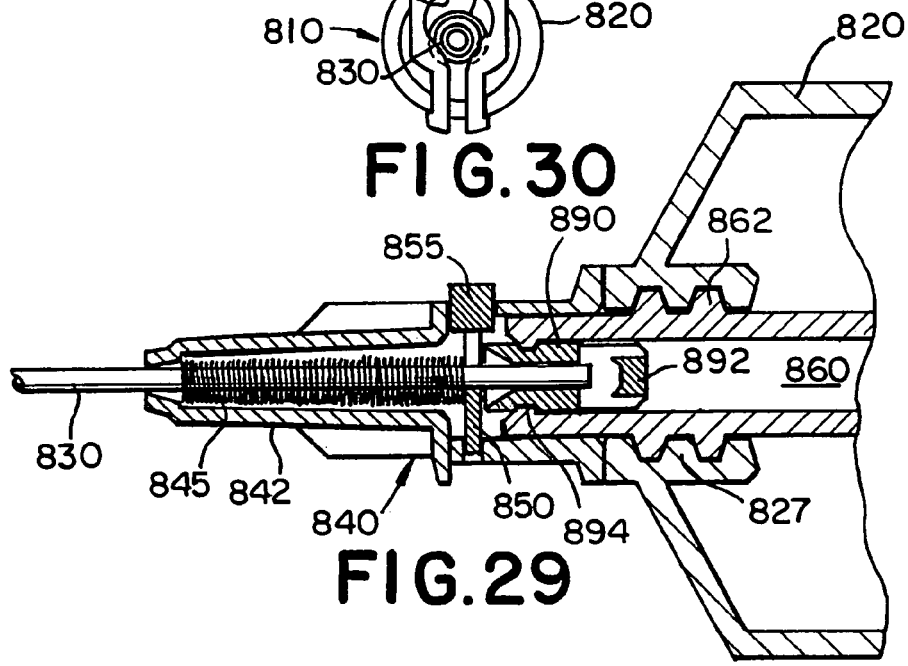
FIG. 29 is an enlarged fragmentary view of the fluid collection device illustrated in FIG. 27.

The front needle 835 is operable between an extended position and a retracted position. The needle assembly 840 includes a spring 845 disposed around the front needle 830 and connected to the front needle. The spring 845 biases the front needle 830 rearwardly toward the retracted position. A latch 850 engages the spring 845 to releasably retain the front needle in the extended position. The latch 850 includes an aperture 852 through which the front needle extends. As shown in FIG. 30, the aperture 852 is eccentric with the front needle 830 and the spring 845, so that in the latched position the spring abuts the latch. In this way, the latch 850 retains the front needle 830 against being propelled rearwardly. As described above, the spring engages the latch 850 in the latched position. Alternatively, the front needle 830 can include a circumferential flange or block bonded to the needle, which engages the latch.

An actuation button 855 is connected to the latch 850. Depressing the actuation button displaces the latch to an unlocked position in which the aperture 852 is aligned with the spring 845. In this unlocked position, the spring 845 passes through the aperture 852, so that the spring propels the front needle 830 rearwardly into the retracted position. As shown in FIG. 28, the front needle 830 is retracted into the conduit 860.

Preferably, the needle assembly 840 is releasably connectable to the barrel 820. In the present instance, the conduit 860 includes external threads 862 that mate with the internal threads 827 at the forward end 826 of the barrel. In this way, the entire needle assembly 840 along with the retracted front needle 830 can be removed from the barrel 820 after fluid has been collected. The barrel 820 can then be reused with a new needle assembly 840.

The device 810 preferably incorporates a member for preventing residual fluid from being ejected from the front needle 830 during retraction. The rear portion of needle 830 extends into the forward portion of the conduit 860. A plug support member 890 is positioned in the conduit 860 on the front needle 830 to hold a plug 892 in axial alignment with the rear end of the needle. When the front needle 830 is retracted, the open rearward end of the front needle is driven into abutting contact with the plug, sealing the rearward end of the needle. The front needle 830, plug 892 and support member 890 then retract together into the conduit. As the front needle travels rearwardly, the plug remains on the rear of the end the front needle to provide a partial vacuum in the rear portion of the rearwardly-accelerating needle. Thus, residual fluid is retained in the front needle.

Figure 31:
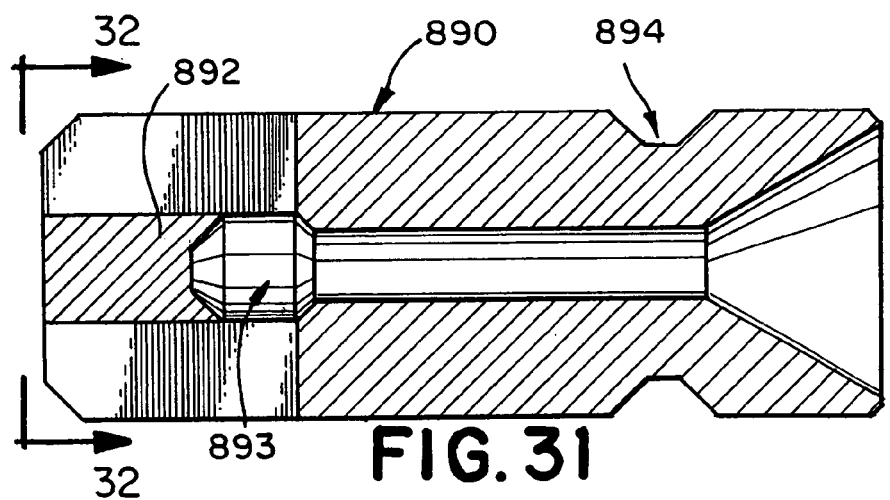
FIG. 31 is a sectional view of a plug support member for providing an anti-fluid ejection mechanism for the device illustrated in FIG. 27.
Figure 32:
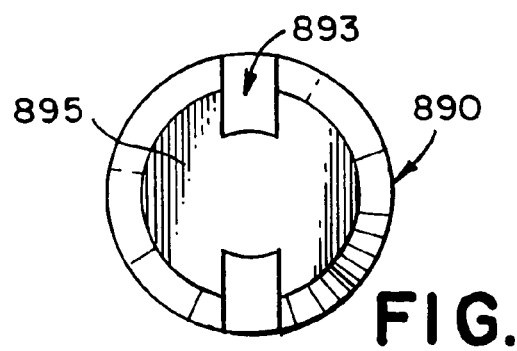
FIG. 32 is a rear elevational view of the plug support member of FIG. 31 from the perspective 32-32 in FIG. 31.

Referring now to FIG. 31, the plug 892 and the plug support member 890 are preferably integrally formed of an elastomeric material. The plug support member 890 preferably has a waist 894 formed about its exterior for engaging a complementary interior surface of the conduit 860. Additionally, the plug support member has an axial cavity formed therein for receiving and holding the rear portion of the forward needle 830 during assembly of the device 810. As can be seen in FIG. 32, the plug 892 is supported by a web 895, which forms the rear portion of the plug support member 890. The web 895 includes opening 893 formed therein to provide a fluid flow path through the rear portion of the plug support member 890 contiguous with the central cavity thereof. When the needle is retracted, the needle is driven into engagement with the plug 892. The waist 894 provides sufficient retention force so that the front needle 830 travels relative to the plug support member 890 until the needle engages the plug. After the front needle engages the plug, the continued rearward motion of the needle causes the support member 890 to release from the conduit so that the needle, plug and support member travel rearwardly together.

Configured in this way, the device 810 operates as follows. The front needle 830 is inserted into a patient. A fluid collection container such as a vacuum tube 880 is then inserted into the open end 824 of the barrel 820. The vacuum tube is sealed by a resealable plug 882. The rear needle 835 pierces the resealable plug 882 of the vacuum tube 880 so that the vacuum tube is in fluid communication with the front needle 830. In this way, fluid flows from the front needle 830 into the vacuum tube. After the vacuum tube is filled, the vacuum tube is removed from the open end 824 of the barrel 820. If desired, another vacuum tube can be inserted so that additional fluid can be collected. After the operator has collected sufficient fluid from the patient, the front needle 830 is withdrawn from the patient. The operator then depresses the actuation button 855 to retract the needle. The spring 845 propels the front needle rearwardly into the conduit 860 so that the sharpened tip of the needle is enclosed within the device 810. The device 810 can then be safely discarded, or the needle assembly 840 with the retracted front needle 830 can be removed from the barrel 820 and the barrel can be reused with a new needle assembly.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention. For example, the conduit 860 and tip 842 can be integrally formed with the barrel 820.

The invention claimed is:
1. A medical device, comprising:
a housing having an aperture in a wall of the housing, the aperture defined by a rim;
a first needle having a sharpened tip, the first needle operable between an extended position in which the sharpened tip is exposed and a retracted position in which the sharpened tip is shielded;
a biasing element biasing the first needle toward the retracted position;

a needle hub displaceable between a forward position in which the first needle is in the extended position and a rearward position in which the first needle is in the retracted position, the needle hub comprising:
- a first connector at an end of the hub, the first connector configured to provide a fluid-tight connection between a fluid line and the first needle;
- a radially deformable arm;
- an actuator disposed at an end of the arm, wherein the actuator is configured to cooperate with the rim of the housing to releasably retain the first needle in the extended position against a bias provided by the biasing element, wherein the actuator is configured to be moved out of cooperative engagement with the rim, thereby permitting the biasing element to transition the needle hub to the rearward position, wherein the actuator comprises a forward stop; and
- a flange projecting outwardly from the needle hub at a position forward of the actuator; and
- a lip projecting radially inwardly from the wall of the housing so as to define a contracted opening, wherein the flange of the needle hub is larger in diameter than the opening defined by the lip of the housing such that a rearward edge of the flange can contact the lip, wherein, when the needle hub is transitioned from the forward position to the rearward position, the lip of the housing displaces the actuator radially inwardly such that the actuator passes rearwardly beyond the lip, and wherein, when the needle hub is in the rearward position, the forward stop of the actuator cooperates with a rearward surface of the lip of the housing to prevent forward movement of the needle hub relative to the housing, and the lip cooperates with the flange of the needle hub to impede rearward axial movement of the needle hub beyond the rearward position.

2. The medical device of claim 1, wherein a forward edge of the actuator forms the forward stop.

3. The medical device of claim 1, further comprising a pair of substantially planar wings connected to the housing, the wings projecting outwardly from the housing and being displaceable about a longitudinal axis of the housing.

4. The medical device of claim 3, wherein at least a portion of the wings are disposed forwardly of the aperture in the housing.

5. The medical device of claim 1, wherein a majority of the needle hub is disposed outside the housing when the needle hub is in the rearward position.

6. The medical device of claim 1, wherein the opening defined by the lip of the housing is larger than a body of the needle hub and smaller than the flange of the needle hub such that in the rearward position, the needle hub extends through the opening.

7. The medical device of claim 1, further comprising:
- a fluid line connectable with the first connector, the fluid line comprising a second connector;
- a second hollow housing connectable with the second connector, the second housing having a generally open rearward end for receiving a specimen container that is sealed by a pierceable seal; and
- a second needle attached to the second housing and having a sharpened tip projecting into the interior of the second housing, the second needle operable to pierce the pierceable seal.

8. The medical device of claim 1, wherein the actuator is recessed relative to an outer surface of the housing when the needle hub is in the forward position.

9. The medical device of claim 1, wherein the deformable arm is configured to move from a retaining position in which the actuator cooperates with the rim of the aperture in the wall of the housing to an actuated position in which the needle hub is permitted to transition to the rearward position, wherein the actuated position is closer to a longitudinal axis of the needle hub than is the retaining position.

10. The medical device of claim 9, wherein the biasing element has a biasing force between a lower limit and an upper limit, the lower limit being defined by an amount of axial force required to effectuate inward displacement of the actuator due to interaction between the actuator and the lip of the housing during transition of the needle hub from the forward position to the rearward position, the upper limit being defined by an amount of axial force required to overcome the cooperation between the lip of the housing and the flange of the needle hub to impede rearward axial movement of the needle hub beyond the rearward position.

11. The medical device of claim 1, wherein the biasing element has a biasing force between a lower limit and an upper limit, the lower limit being defined by an amount of axial force required to effectuate inward displacement of the actuator due to interaction between the actuator and the lip of the housing during transition of the needle hub from the forward position to the rearward position, the upper limit being defined by an amount of axial force required to overcome the cooperation between the lip of the housing and the flange of the needle hub to impede rearward axial movement of the needle hub beyond the rearward position.

12. The medical device of claim 1, wherein the actuator comprises a surface that is directly manually operable from outside the housing.

13. The medical device of claim 1, wherein the actuator is outside of the housing and is rearward of the housing when the needle hub is in the rearward position.

14. The medical device of claim 1, wherein the actuator is configured to move outwardly as the needle hub is moved into the rearward position.

15. The medical device of claim 1, wherein the flange projecting outwardly from the needle hub is spaced from the forward stop of the needle hub such that a portion of the housing can be received between the flange and the forward stop when the needle hub is in the rearward position.

16. The medical device of claim 1, wherein the actuator is configured to be displaced radially inwardly so as to be moved out of cooperative engagement with the rim of the housing to thereby permit the needle hub to transition from the forward position to the rearward position without radial flexing of the flange.

17. A method for drawing fluid from a patient, the method comprising:
- providing the medical device of claim 7;
- attaching the fluid line to the first connector;
- attaching the second connector to the second housing;
- inserting the first needle into a patient;
- inserting a specimen container that includes a pierceable seal into the second housing so that the second needle pierces the pierceable seal; and
- moving the first needle to the retracted position.

18. The method of claim 17, further comprising:
- withdrawing the specimen container from the second housing;
- providing a second container having a pierceable seal; and
- inserting the second specimen container into the second housing so that the second needle pierces the seal of the second specimen container and the second specimen container is in fluid communication with the first needle.

* * * * *